(12) United States Patent
Carrasco et al.

(10) Patent No.: US 9,518,300 B2
(45) Date of Patent: Dec. 13, 2016

(54) COMPOSITION AND METHOD FOR TREATING A HEMATOLOGICAL MALIGNANCY

(71) Applicant: Dana-Farber Cancer Institute, Inc., Boston, MA (US)

(72) Inventors: Ruben Carrasco, Brookline, MA (US); Jianjun Zhao, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 14/686,036

(22) Filed: Apr. 14, 2015

(65) Prior Publication Data

US 2015/0313932 A1 Nov. 5, 2015

Related U.S. Application Data

(60) Provisional application No. 61/979,051, filed on Apr. 14, 2014.

(51) Int. Cl.
| | | |
|---|---|---|
| *A61K 48/00* | (2006.01) | |
| *C07H 21/02* | (2006.01) | |
| *C07H 21/04* | (2006.01) | |
| *C12Q 1/68* | (2006.01) | |
| *C12N 15/113* | (2010.01) | |
| *A61K 45/06* | (2006.01) | |
| *A61K 9/14* | (2006.01) | |
| *A61K 9/00* | (2006.01) | |
| *A61K 31/7105* | (2006.01) | |
| *A61K 31/711* | (2006.01) | |
| *A61K 31/663* | (2006.01) | |

(52) U.S. Cl.
CPC ........... *C12Q 1/6886* (2013.01); *A61K 9/0019* (2013.01); *A61K 9/145* (2013.01); *A61K 31/663* (2013.01); *A61K 31/711* (2013.01); *A61K 31/7105* (2013.01); *A61K 45/06* (2013.01); *C12N 15/113* (2013.01); *C12N 15/1135* (2013.01); *C12N 2310/14* (2013.01); *C12N 2310/141* (2013.01); *C12N 2310/321* (2013.01); *C12N 2320/31* (2013.01); *C12Q 2600/118* (2013.01); *C12Q 2600/178* (2013.01)

(58) Field of Classification Search
CPC .............................. A61K 48/00; C12N 15/113
See application file for complete search history.

(56) References Cited

U.S. PATENT DOCUMENTS 8,071,573 B2 * 12/2011 Sanders ................ C07F 9/3873
435/183

FOREIGN PATENT DOCUMENTS

WO WO 2007/033023 A2 * 3/2007 ............. A61K 48/00

OTHER PUBLICATIONS

Zhao et al., "miR-30-5p Functions as a Tumor Suppressor and Novel Therapeutic Tool by Targeting the Oncogenic Wnt/β-Cantenin/BCL9 Pathway," Cancer Res. (74(6); 1801-13 (2014).
Kao et al., "miR-30 as a Tumor Suppressor Connects EGF/Src Signal to ERG and EMT," Oncogene (2013) pp. 1-9.
Yu et al., "Mir-30 Reduction Maintains Self-Renewal and Inhibits Apoptosis in Breast Tumor-Initiating Cells," Oncogene (2010) 29, 4194-4204.

* cited by examiner

*Primary Examiner* — Amy Bowman
(74) *Attorney, Agent, or Firm* — Lathrop & Gage LLP

(57) ABSTRACT

Provided are compositions and methods for treating hematological malignancies, such as multiple myeloma, in a subject by increasing levels or activity of miR-30 RNA in plasma cells of the subject.

31 Claims, 27 Drawing Sheets

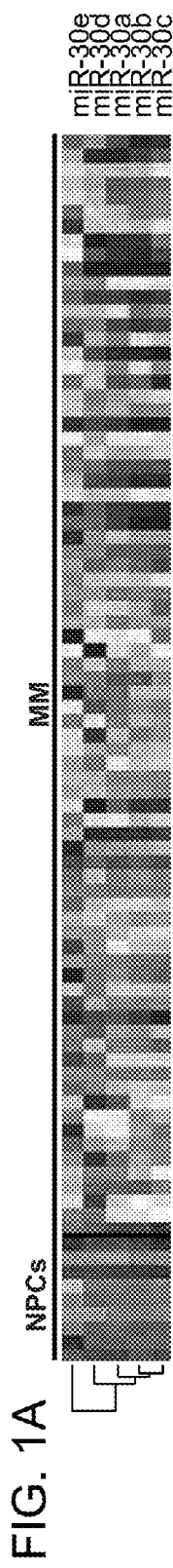
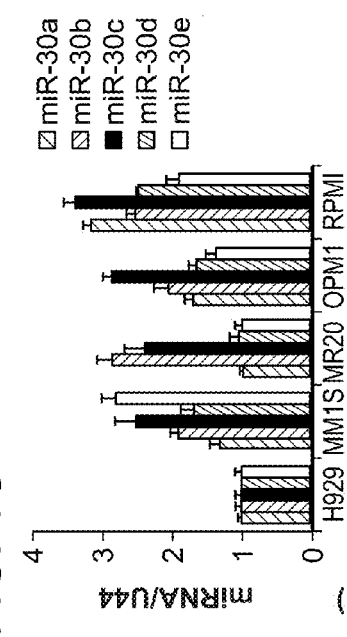
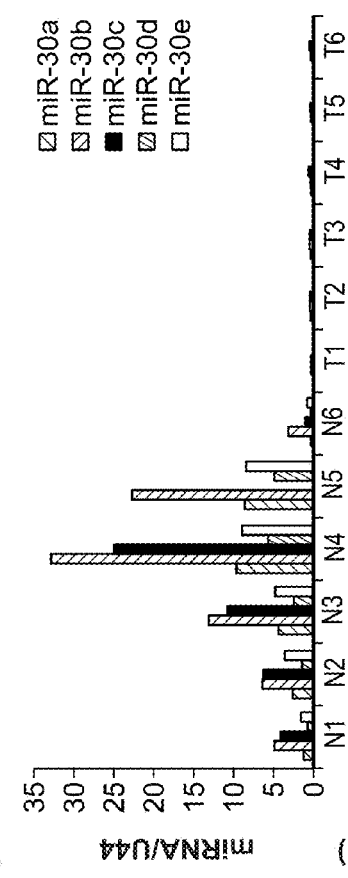
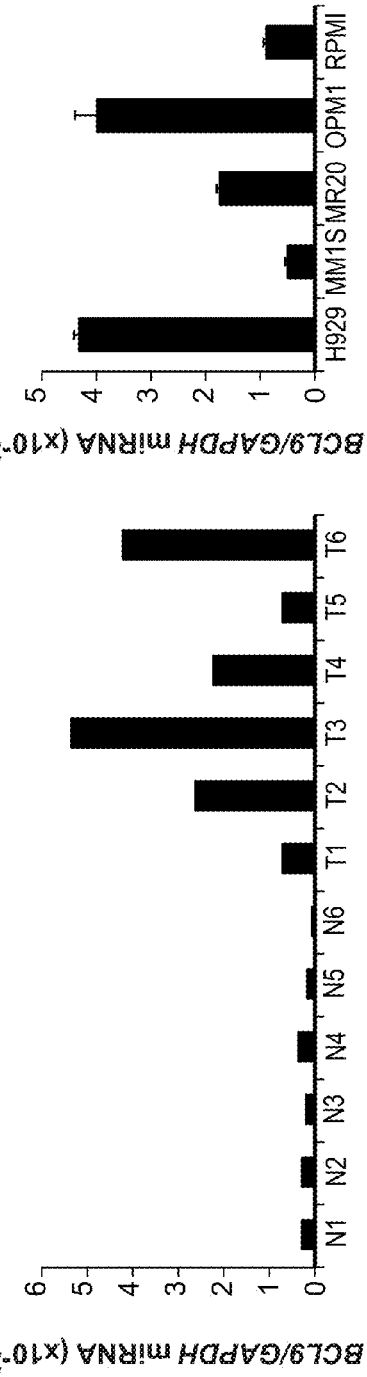
FIG. 1A  FIG. 1B  FIG. 1C

FIG. 2A

```
(SEQ ID NO:32)  BCL9 3'UTR-mut-1   ...GCACCGUUCUCUGUA------G...
(SEQ ID NO:33)  BCL9 3'UTR-wt-1    ...GCACCGUUCUCUGUAUGUUUACG...
                                                  ||||||
                      miR-30a         GAAGGUCAGCUCCUACAAAUGU (SEQ ID NO:1)
                      miR-30b         UCGACUCACAUCCUACAAAUGU (SEQ ID NO:2)
                      miR-30c         CGACUCUCACAUCCUACAAAUGU (SEQ ID NO:3)
                      miR-30d         GAAGGUCAGCCCCUACAAAUGU (SEQ ID NO:4)
                      miR-30e         GAAGGUCAGUUCCUACAAAUGU (SEQ ID NO:5)
                                                  ||||||
(SEQ ID NO:34)  BCL9 3'UTR-wt-2    ...ACAGGAAUGCUGGGCUGUUUACU...
(SEQ ID NO:35)  BCL9 3'UTR-mut-2   ...ACAGGAAUGCUGGGC------U...
```

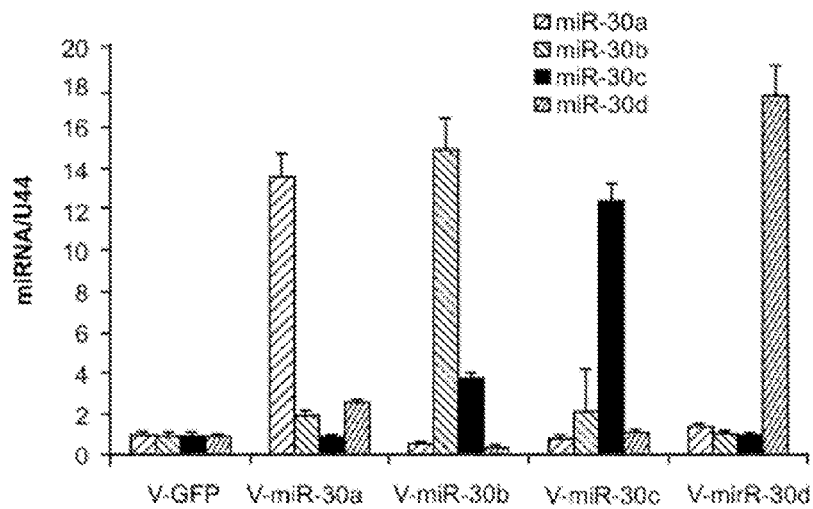

FIG. 2B 293 4d

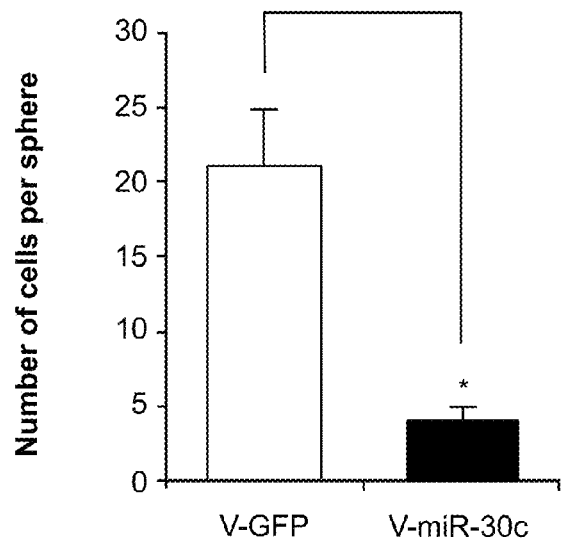
FIG. 5E
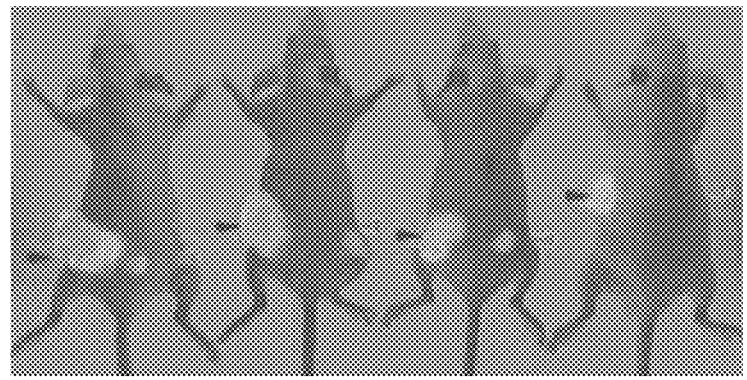
FIG. 6A
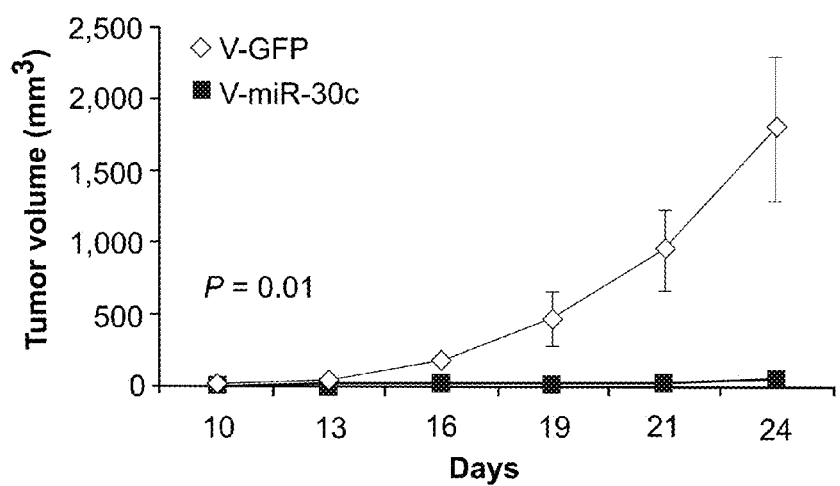

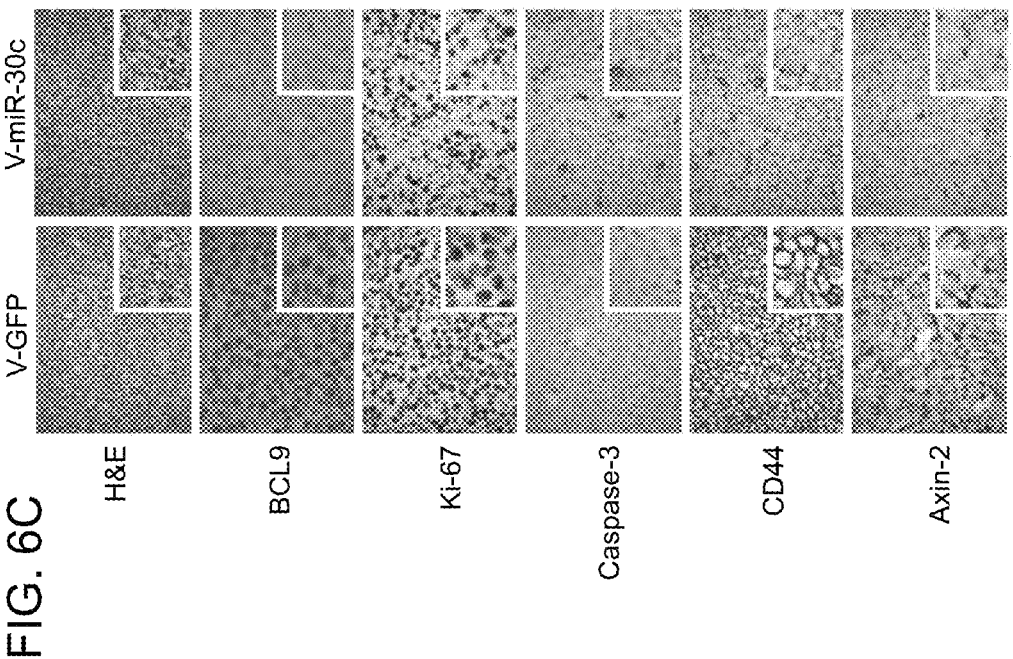
FIG. 6C
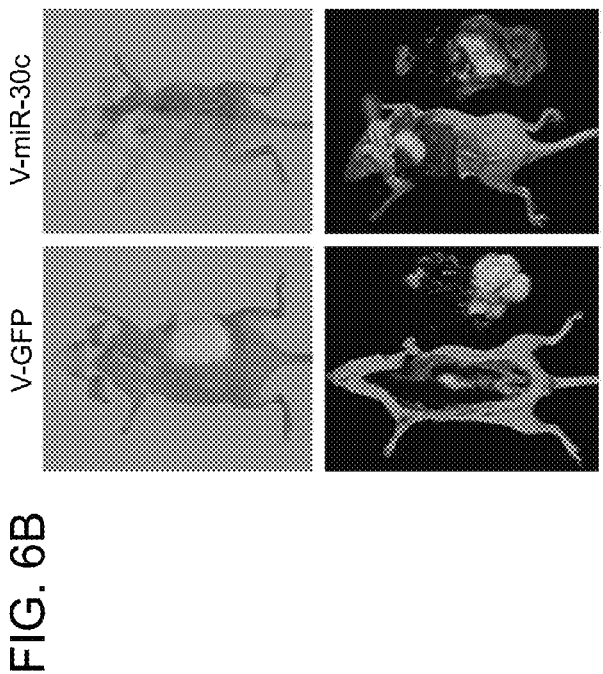
FIG. 6B
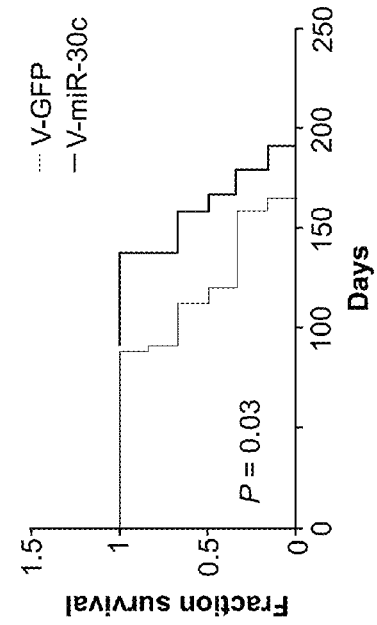

FIG. 8B

| Targetcan | PicTar | miRDB | microCosm |
|---|---|---|---|
| has-miR-181 | has-miR-330 | hsa-miR-330-3p | hsa-miR-593 |
| has-miR-30s | has-miR-32 | hsa-miR-2113 | hsa-miR-30c-2* |
| has-miR-101 | has-miR-92 | hsa-miR-605 | hsa-miR-26b* |
| has-miR-204/211 | has-miR-30s | hsa-miR-188-5p | hsa-miR-186* |
| has-miR-218 | has-miR-218 | hsa-miR-1267 | hsa-miR-30c-1* |
|  | has-miR-140 | hsa-miR-338-5p | hsa-miR-141 |
|  | has-miR-188 | hsa-miR-30s | hsa-miR-450b-5p |
|  | has-miR-22 | hsa-miR-218 | hsa-miR-198 |
|  | has-miR-216 | hsa-miR-509-3-5p | hsa-miR-188-3p |
|  | has-miR-384 | hsa-miR-1228 | hsa-miR-200a |
|  | has-miR-15a/b/16 | hsa-miR-495 | hsa-miR-30s |
|  | has-miR-338 | hsa-miR-509-5p | hsa-miR-26b* |
|  | has-miR-144 | hsa-miR-101 | hsa-miR-188-5p |
|  | has-miR-199a | hsa-miR-200a | hsa-miR-155* |
|  | has-miR-101 | hsa-miR-548s | hsa-miR-575 |
|  | has-miR-186 | hsa-miR-141 | hsa-miR-338-3p |
|  |  | hsa-miR-362-3p | hsa-miR-144 |
|  |  | hsa-miR-22 | hsa-miR-330-3p |
|  |  | hsa-miR-329 | hsa-miR-411 |
|  |  | hsa-miR-625 | hsa-miR-22 |
|  |  |  | hsa-miR-489 |
|  |  |  | hsa-miR-29c* |

FIG. 8C

BCL9      329-335    486-492
          WT-1       WT-2

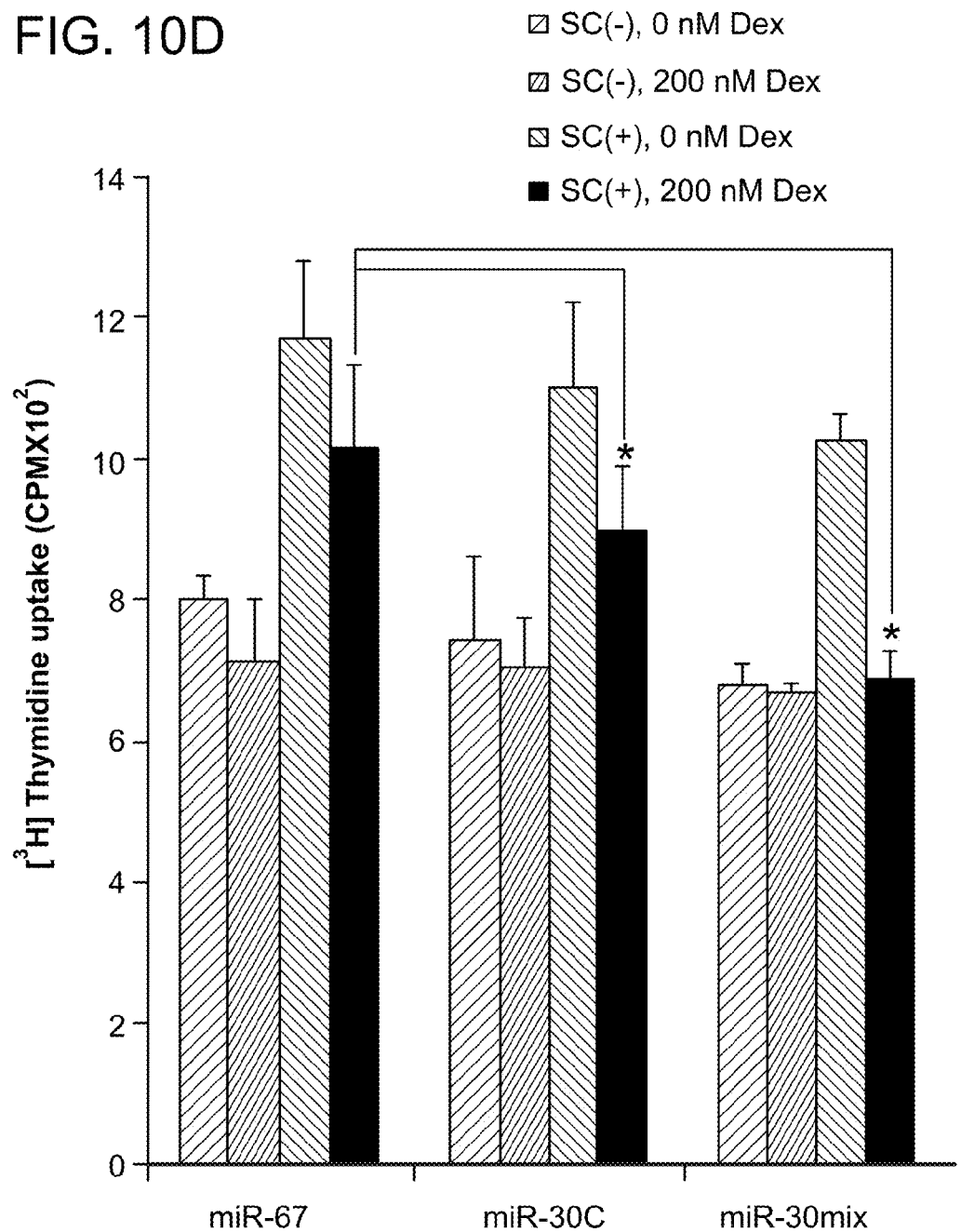

```
                       SEQUENCE LISTING

<160> NUMBER OF SEQ ID NOS: 40

<210> SEQ ID NO 1
<211> LENGTH: 22
<212> TYPE: RNA
<213> ORGANISM: Homo sapiens

<400> SEQUENCE: 1
uguaaacauc cucgacugga ag                                            22

<210> SEQ ID NO 2
<211> LENGTH: 22
<212> TYPE: RNA
<213> ORGANISM: Homo sapiens

<400> SEQUENCE: 2
uguaaacauc cuacacucag cu                                            22

<210> SEQ ID NO 3
<211> LENGTH: 23
<212> TYPE: RNA
<213> ORGANISM: Homo sapiens

<400> SEQUENCE: 3
uguaaacauc cuacacucuc agc                                           23

<210> SEQ ID NO 4
<211> LENGTH: 22
<212> TYPE: RNA
<213> ORGANISM: Homo sapiens

<400> SEQUENCE: 4
uguaaacauc cccgacugga ag                                            22

<210> SEQ ID NO 5
<211> LENGTH: 21
<212> TYPE: RNA
<213> ORGANISM: Homo sapiens

<400> SEQUENCE: 5
uguaaacauc cuugacugaa g                                             21

<210> SEQ ID NO 6
<211> LENGTH: 72
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 6
cgcgttgcca tcggtcatgt gttgcaccgt tctctgtatg tttacgtcct ttggactggc    60
ttctcggatc ca                                                        72

<210> SEQ ID NO 7
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agcttggatc cgagaagcca gtccaaagga cgtaaacata cagagaacgg tgcaacacat    60
gaccgatggc aa                                                        72

<210> SEQ ID NO 8
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgcgttgcca tcggtcatgt gttgcaccgt tctctgtagt cctttggact ggcttctcgg    60
atcca                                                                65

<210> SEQ ID NO 9
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agctggatcc gagaagccag tccaaaggac tacagagaac ggtgcaacac atgaccgatg    60
gcaa                                                                 64

<210> SEQ ID NO 10
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgcgtgtctt tggggcaaga ggagaacagg aatgctgggc tgtttacttt aggtggagaa    60
tccatggatc ca                                                        72

<210> SEQ ID NO 11
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agcttggatc catggattct ccacctaaag taaacagccc agcattcctg ttctcctctt    60
gccccaaaga ca                                                              72

<210> SEQ ID NO 12
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgcgtgtctt tggggcaaga ggagaacagg aatgctgggc tttaggtgga gaatccatgg          60
atcca                                                                      65

<210> SEQ ID NO 13
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agcttggatc catggattct ccacctaaag cccagcattc ctgttctcct cttgccccaa          60
agaca                                                                      65

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tttgcattgc agtcaacagt c                                                    21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgagtccact tggctttctg t                                                    21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cggaaactgt tgacagtgga t                                                    21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 17
ggtgcaaaga catagccaga a                                              21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcaccgtcaa ggctgagaac                                                20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tggtgaagac gccagtgga                                                 19

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 20
aaggcaagcu gacccugaag u                                              21

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 21
cuuccagucg aggauguuua ca                                             22

<210> SEQ ID NO 22
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 22
agcugagugu aggauguuua ca                                             22

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

```
<400> SEQUENCE: 23
gcugagagug uaggauguuu aca                                              23

<210> SEQ ID NO 24
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 24
cuuccagucg gggauguuua ca                                               22

<210> SEQ ID NO 25
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 25
cuuccaguca aggauguuua ca                                               22

<210> SEQ ID NO 26
<211> LENGTH: 24
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 26
ucacaaccuc cuagaaagag uaga                                             24

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 27
uguaaacauc cucgacugga ag                                               22

<210> SEQ ID NO 28
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 28
uguaaacauc cuacacucag cu                                               22

<210> SEQ ID NO 29
<211> LENGTH: 23
<212> TYPE: RNA
<213> ORGANISM: Artificial Sequence
<220> FEATURE:
<223> OTHER INFORMATION: Description of Artificial Sequence: Synthetic
      primer
```

<400> SEQUENCE: 29
uguaaacauc cuacacucuc agc                                                 23

<210> SEQ ID NO 30
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 30
uguaaacauc cccgacugga ag                                                  22

<210> SEQ ID NO 31
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 31
uguaaacauc cuugacugga ag                                                  22

<210> SEQ ID NO 32
<211> LENGTH: 16
<212> TYPE: RNA
<213> ORGANISM: Unknown
<220> FEATURE:
<223> OTHER INFORMATION: Description of Unknown: BCL9 3'UTR-mut-1
      oligonucleotide

<400> SEQUENCE: 32
gcaccguucu cuguag                                                         16

<210> SEQ ID NO 33
<211> LENGTH: 23
<212> TYPE: RNA
<213> ORGANISM: Unknown
<220> FEATURE:
<223> OTHER INFORMATION: Description of Unknown: BCL9 3'UTR-wt-1
      oligonucleotide

<400> SEQUENCE: 33
gcaccguucu cuguauguuu acg                                                 23

<210> SEQ ID NO 34
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
uguaaacauc cucgacugga ag                                                  22

<210> SEQ ID NO 35
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35

```
uguaaacauc cuacacucag cu                                            22

<210> SEQ ID NO 36
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uguaaacauc cuacacucuc agc                                           23

<210> SEQ ID NO 37
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
uguaaacauc cccgacugga ag                                            22

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uguaaacauc cuugacugaa g                                             21

<210> SEQ ID NO 39
<211> LENGTH: 23
<212> TYPE: RNA
<213> ORGANISM: Unknown
<220> FEATURE:
<223> OTHER INFORMATION: Description of Unknown: BCL9 3'UTR-wt-2
      oligonucleotide

<400> SEQUENCE: 39
acaggaaugc ugggcuguuu acu                                           23

<210> SEQ ID NO 40
<211> LENGTH: 16
<212> TYPE: RNA
<213> ORGANISM: Unknown
<220> FEATURE:
<223> OTHER INFORMATION: Description of Unknown: BCL9 3'UTR-mut-2
      oligonucleotide

<400> SEQUENCE: 40
acaggaaugc ugggcu                                                   16
```

COMPOSITION AND METHOD FOR TREATING A HEMATOLOGICAL MALIGNANCY

CROSS REFERENCE TO RELATED APPLICATION

This application claims priority to U.S. Ser. No. 61/979,051, filed on Apr. 14, 2014, the contents of which are hereby incorporated by reference in their entirety.

STATEMENT AS TO GOVERNMENTALLY SPONSORED RESEARCH

This invention was made with U.S. government support under NIH Grant 1R01CA151391. The government has certain rights in the invention.

SEQUENCE LISTING

The instant application contains a Sequence Listing which has been submitted electronically in ASCII format and is hereby incorporated by reference in its entirety. Said ASCII copy, created on Jun. 18, 2015, is named 50083-002001_SL.txt and is 9,556 bytes in size.

BACKGROUND

The invention relates to compositions and methods for treating hematological malignancies, including multiple myeloma.

Multiple myeloma is a cancer of plasma cells that accumulate in the bone marrow. Multiple myeloma remains uncurable despite recent advances in understanding its molecular pathogenesis and the development of promising new therapies.

The canonical Wnt pathway is constitutively active in multiple myeloma and promotes tumor cell proliferation and disease progression; however, mutations in Wnt pathway members APC, Axin or β-catenin have not been reported. Instead, the mechanism of pathologic Wnt signaling in multiple myeloma has been linked to post-transcriptional regulation of β-catenin and/or increased levels of BCL9, implicating the β-catenin co-factor as a bona fide oncogene.

The Wnt/β-catenin signaling pathway is implicated in the pathogenesis of a broad range of cancers and has emerged as a promising target for therapy. Loss-of-function mutations in APC and Axin, as well as activating mutations in β-catenin itself, facilitate β-catenin nuclear translocation and drive oncogenic Wnt transcription.

SUMMARY

The invention is based in part on the discovery that downregulation of the tumor suppressor microRNA miR-30-5p is a frequent pathogenetic event in multiple myeloma. The inventors have discovered that miR-30-5p downregulation occurs as a result of an interaction between multiple myeloma (MM) cells and bone marrow stromal cells, which, in turn, enhances expression of BCL9, a transcriptional co-activator of the Wnt signaling pathway known to promote MM cell proliferation, survival, migration, drug resistance and formation of MM cancer stem cells.

In one aspect, the invention provides a method for treating a subject at risk for or having multiple myeloma (MM) by administering to a subject in need thereof a therapeutically effective amount of an agent that increases levels or activity of miR-30 RNA in the subject. In some embodiments, multiple myeloma cells of the subject are sensitive to inhibition of aWnt signaling pathway.

In some embodiments, administration of the agent decreases BCL9 expression in plasma cells of the subject. In some embodiments, the agent is a miR-30 RNA or a polynucleotide (DNA or RNA) encoding a miR-30 RNA. In some embodiments, the agent has one or more non-naturally occurring nucleotides, e.g., one or more 2'-O-methyl oligoribonucleotides, locked nucleic acid (LNA) modified oligoribonucleotides, or hybridized forms of oligoribonucleotides.

In some embodiments, the agent comprises polynucleotides that hybridize specifically to sequence motifs d \wt-1 (9129-9135 bp) and wt-2 (9880-9886 bp) in a 3'LTR of BCL9 mRNA. In some embodiments, the agent is a polynucleotide sequence with one or insertions, deletions, or substitutions in a miR-30 reference sequence.

In some embodiments, the agent comprises the nucleotide sequence of one or more of a miR-30a, miR-30b, miR-30c, miR-30d, miR-30e, or miR-30s RNA.

In some embodiments, the agent comprises miR-30a, miR-30b, miR-30c, miR-30d, miR-30e, and miR-30s RNA. In some embodiments, the agent is provided in a lipid, a nanoparticle, aptamer linked oligoribonucleotides or a lipid nanoparticle.

In some embodiments, the agent is provided in a viral vector, e.g., a lenti-viral vector, adenoviral vector, adeno-associated vector, or retroviral vector. In some embodiments, the agent is provided in a plasmid. In some embodiments, the agent is administered intravenously, intraperitoneally, or subcutaneously. In some embodiments, the subject has or is at risk for monoclonal Gammopathy of Undetermined Significance (MGUS), smoldering myeloma, asymptomatic multiple myeloma (MM), or symptomatic MM. The symptomatic MM can be, e.g., newly diagnosed MM or late stage relapsed/refractory MM.

In some embodiments, the method includes administering an additional anti-cancer therapy to the individual. The additional anti-cancer therapy can be, e.g., surgery, chemotherapy, radiation, hormone therapy, immunotherapy, or a combination thereof. In some embodiments, the additional anti-cancer therapy reduces bone absorption e.g., osteoclast mediated bone resorption. The additional anti-cancer therapy can be, e.g., bisphosphonate.

In some embodiments, the subject is a human.

In another aspect, the invention provides a method of reducing proliferation, survival, migration, or colony formation ability of multiple myeloma cells in a subject with multiple myeloma. The method includes administering to the subject a therapeutically effective amount of an agent that increases levels or activity of miR-30 RNA in the subject.

In a further aspect, the invention provides a method of inhibiting metastasis of myeloma in a subject, the method comprising administering to a subject with myeloma a therapeutically effective amount of an agent that increases levels or activity of miR-30 RNA in the subject.

In a still further aspect, the invention provides method of treating a hematological malignancy by administering to a subject in need thereof a therapeutically effective amount of an agent that increases levels or activity of miR-30 RNA in the subject.

In some embodiments, the hematological malignancy is myelodysplastic syndrome, Hodgkin's lymphoma, chronic lymphocytic leukemia, or B cell lymphoma.

In another aspect, the invention provides a method of diagnosing multiple myeloma in a subject. The method includes obtaining plasma cells from the subject and determining levels of miRNA-30 in the plasma cells. A decreased copy number of the miRNA-30 compared to the amount of the miR-30 RNA in a plasma cell of control cells not having multiple myeloma or an associated condition indicates that the subject has multiple myeloma. The levels of miRNA-30 can be determined using, e.g., fluorescence in situ hybridization.

In another aspect, the invention provides a method for determining the prognosis of a multiple myeloma patient. The method comprises obtaining plasma cells from the patient and determining levels of miRNA-30 in the plasma cell. A decreased copy number of the miRNA-30 compared to the amount of the miR-30 RNA in a plasma cell of control cells not having multiple myeloma or an associated condition indicates that the subject has a poor prognosis. In some embodiments, the copy number of the miRNA-30 is determined by fluorescence in-situ hybridization.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention are apparent from the following description, and from the claims.

BRIEF DESCRIPTION OF THE DRAWINGS

FIGS. 1A-E show that miR-30s are downregulated in multiple myeloma (MM).

FIG. 1A is a heatmap of hierarchical cluster analysis of miR-30s expression in a patient's multiple myeloma cells and normal plasma cells (NPC).

FIGS. 1B-D show qRT-PCR analysis of miR-30s and BCL9 mRNA expression in normal plasma cells (N1-N6), patient's multiple myeloma cells (T1-T6; B), and multiple myeloma cell lines (C). (D), analysis of miR-30s and BCL9 mRNA expression levels in patient's multiple myeloma cells from published dataset GSE27306 (miR-30a, P=0.030; miR-30b, P=0.007; miR-30c, P=0.001; miR-30d, P=0.028; miR-30e, P=0.050).

FIG. 1E shows two of six representative cases of ISH (left) and IHC (right) analysis of miR-30s and BCL9 expression levels in multiple myeloma patient's bone marrow.

FIGS. 2A-E show that miR-30s targets BCL9 mRNA.

FIG. 2A is a sequence alignment of miR-30a, b, c, d, e, with the seed binding sequences on the 3'UTR regions of BCL9 mRNA. The sequences of miR-30a, b, c, d, e are read from right to left and correspond to SEQ ID NOs: 1, 2, 3, 4, 5, respectively. These sequences are aligned with two sequence motifs in human Bcl-9 3'UTR, designated as wt-1 (SEQ ID NO: 33) and wt-2 (SEQ ID NO: 34), and corresponding mutants mut-1 (SEQ ID NO: 32) and mut-2 (SEQ ID NO: 35) wherein a sequence complementary to the "seed" sequence of the miR-30 family members (5'-gtaaaca-3'; SEQ ID NO: 36) is removed.

FIG. 2B shows qRT-PCR verification of induced ectopic expression of miR-30s members in H929 cells after transduction of V-GFP or each miR-30s member.

FIGS. 2C-E show that ectopic expression of each miR-30s member is associated with a reduction in BCL9 mRNA (C) and protein (D) levels. *, P<0.05. (E), luciferase reporter assays in HEK293T cells transduced with GFP or each miR-30s member. pmiR-0 (empty reporter plasmid), pmiR-BCL9-30-wt-1 (reporter plasmid containing wt-1), pmiR-BCL9-30-wt-2 (reporter plasmid containing wt-2), pmiR-BCL9-30-mut-1 (reporter plasmid containing mut-1), or pmiR-BCL9-30-mut-2 (reporter plasmid containing the mut-2). *, P<0.05.

FIG. 3A shows qRT-PCR verification of induced ectopic expression of miR-30 members in H929 cells after transduction of V-GFP or each miR-30s member.

FIGS. 3B-3D show that ectopic expression of miR-30c reduces mRNA levels of BCL9, as well as the Wnt target genes Axin-2 and CD44 but not GAPDH. Ectopic expression of miR-30s member reduces protein levels of BCL9 as evaluated by immunoblot (C) and immunofluorescence (D) studies. *, P<0.05.

FIG. 3E shows Wnt reporter activity in H929 cells stably transduced with V-miR-30c or control V-GFP. *, P<0.01.

FIG. 3F: RPMI8226 cells were transduced with Cel-miR-67 control or increased concentrations of mature miR-30c, and levels of miR-30c and BCL9 protein were measured by qRT-PCR (top) or immunoblot analysis (bottom), respectively.

FIG. 3G shows immunofluorescence analysis of BCL9, CD44, and Axin-2 expression (top) as well as [$^3$H] thymidine uptake (bottom) of multiple myeloma patient CD138$^+$ cells transduced with Cel-miR-67 or has-miR-30c. *, P<0.05.

FIG. 4A: [$^3$H] thymidine uptake of H929 and OPM1 cells transduced with V-GFP or V-miR-30c. *, P<0.05.

FIG. 4B shows representative images of colony formation assay of H929 cells transduced with V-GFP or V-miR-30c. Insets, morphology of the spheres under light and florescence microscopy. Numbers of colonies per well are expressed as means. *, P<0.01.

FIG. 4C shows invasion and migration ability of H929 cells stably transduced with V-GFP or V-miR-30C. *, P<0.01.

FIG. 4D shows flow cytometry analysis of Annexin V and propidium iodine (PI) staining of H929 cells transduced with V-GFP or V-miR-30C. The y-axis represents PI staining (10,000 cells) and the x-axis represents Annexin V staining (right). Data as percentages from triplicate experiments are also shown (left). *, P<0.05.

FIGS. 5A-E show that miR-30c decreases the population of multiple myeloma cancer stem cells.

FIGS. 5A and 5B show a side population fraction of H929 cells transduced with V-GFP or V-miR-30c, as detected by functional Hoechst 33342 stem cell staining assay. Verapamil is used as an inhibitor of side population cells.

FIG. 5C is a representative phase contrast (left) and fluorescence microscopy images (right) of cell spheres formed after culture of side population cells isolated from H929 cells transduced with either V-GFP or V-miR-30c in stem cell medium.

FIG. 5D and FIG. 5E show sphere numbers per 1,000 sorted side population cells (FIG. 5D) and numbers of cells per sphere (FIG. 5E) in cells transduced with V-GFP or V-miR-30c.

FIGS. 6A-6D show that miR-30c inhibits cell proliferation, invasion, and migration, and induces apoptosis, in mouse xenograft models of multiple myeloma.

FIG. 6A, is a representative image of tumors (top) and tumor growth curves (bottom) of NOD/SCID mice (n=8) subcutaneously injected with $5 \times 10^6$ H929 cells transduced with V-GFP or V-miR-30c. Tumor size was evaluated over time by fluorescence whole body imaging. P<0.01.

FIG. 6B shows tumor burden and metastasis (top) and survival (bottom) of NOD/SCID mice (n=6) intravenously injected with $1 \times 10^6$ H929 cells transduced with V-GFP or V-miR-30c. Tumor burden and spread were evaluated over time by fluorescence whole body imaging. P=0.03.

FIG. 6C is an IHC analysis of BCL9, Ki-67, caspase-3, CD44, and Axin-2 expression on tissue sections of GFP-labeled tumor isolated from mice injected with H929 cells transduced with V-GFP or V-miR-30c.

FIG. 6D is D qRT-PCR of miR-30c (top), and immunoblot of BCL9 protein (bottom) expression levels in H929 cells transduced with V-GFP or V-miR-30c and isolated from mice injected subcutaneously (#1 and #2) or intravenously (#3 to #6).

FIG. 7A shows qRT-PCR expression analysis of miR-30.

FIG. 7B shows immunoblot analysis of BCL9 expression in H929 cells transduced with control mature cel-miR-67 (miR-67), each individual miR-30 family member (miR-30s) or an equimolar mixture (miR-30 mix) using RNA-LANCErII.

FIG. 7C shows GSE analysis of genes downregulated by miR-30 mix and shBCL9 treatment in H929 cells.

FIG. 7D shows Kaplan-Meier survival plots of mice treated with control or miR-30 mix after injection of MM1S-Luc-Neo cells.

FIG. 7E is a photomicrograph showing that mice treated with miR-30mix show decreased tumor burden.

FIG. 7F are photomicrographs showing metastasis to the kidney (FIG. 7F, top panel), as well as decreased expression of BCL9 and CD44 proteins (FIG. 7F, bottom panel) and confirmation of in vivo delivery of miR-30s to target cells using miR LNA-ISH (FIG. 7F, second row, bottom panel).

FIG. 7G is a schematic showing how miR-30 interacts with a multiple myeloma cell and bone marrow stromal cell.

FIGS. 8A-E show that MiR-30s target BCL9 in MM cells.

FIG. 8A shows that a positive but weak relationship between DNA copy number and BCL9 expression was observed (Pearson correlation coefficient=0.35, nominal P value=0.0002) in 92 MM patients in whom both CGH and expression data were available.

FIG. 8B shows that miR-30s is the only common miRNA targeting BCL9 mRNA, as predicted by four different web-based softwares including RNA22, DIANA, picTAR, and Targetscan.

FIG. 8C shows that the 3'UTR of BCL9 mRNA was found to contain 2 sequence motifs wt-1 (9129-9135 bp) and wt-2 (9880-9886 bp), which perfectly match the "seed" sequence of the miR-30s family members.

FIG. 8D shows that ectopic expression of miR-30c by V-miR-30c stable infection reduces protein levels of BCL9 as compared with control V-GFP cells when evaluated by western blot analysis in OPM1 and MM1S cells.

FIG. 8E is an immunohistochemical analysis of BCL6 expression on tissue sections of GFP-labeled tumor isolated from mice injected with V-miR-30c or VGFP H929 transduced cells.

FIG. 9A shows Q-RT-PCR analysis of miR-30a/b/c/d/e in MM1S cells treated with scrambled or 2'O-me anti-pan-miR-30 oligonucleotides.

FIGS. 9B and 9C show that BCL9, Axin-2 and CD44 mRNA (FIG. 9B) and BCL9 protein (9C) levels were enhanced in miR-30-knockdown cells as compared to cells treated with scrambled oligonucleotides. * p<0.05.

FIG. 9D shows that Top activity was also increased in miR-30-knockdown cells compared with scrambled cells. Fop activity was not changed. * p<0.05. Top activity was also increased in miR-30-knockdown cells compared with scrambled cells. Fop activity was unchanged. * p<0.05.

FIGS. 10A-D are histograms showing that BMSCs decrease miR-30s levels and that enforced expression of miR-30s inhibits CAM-DR in MM cells.

FIGS. 10A and 10B. show that co-culture of GFP labeled H929 MM cells (V-GFP) with BMSC HS-5 (dsRed) for 48 h promotes downregulation of miR-30s (FIG. 10A) and up-regulation of BCL9, Axin2 and CD44 mRNAs (FIG. 10B). All experiments were performed in triplicate and repeated twice. * p<0.05.

FIGS. 10C and 10D show that enforced overexpression of miR-30c or miR-30 mix (FIG. 10C) reverses the chemoprotective effect of primary BMSCs to against dexamethasone treatment in H929 cells (FIG. 10D). * p<0.05.

FIGS. 11A and B are imaging and histological analyses on L4-L6 vertebrae of the spine showing that no major differences were detected in bone lytic lesions, (FIG. 11C) trabecular bone volume fraction (FIG. 11D, top) and cortical void fraction (FIG. 11D, bottom) between mice treated with vehicle and mice treated with miR-30mix.

DESCRIPTION

Figure 1D:
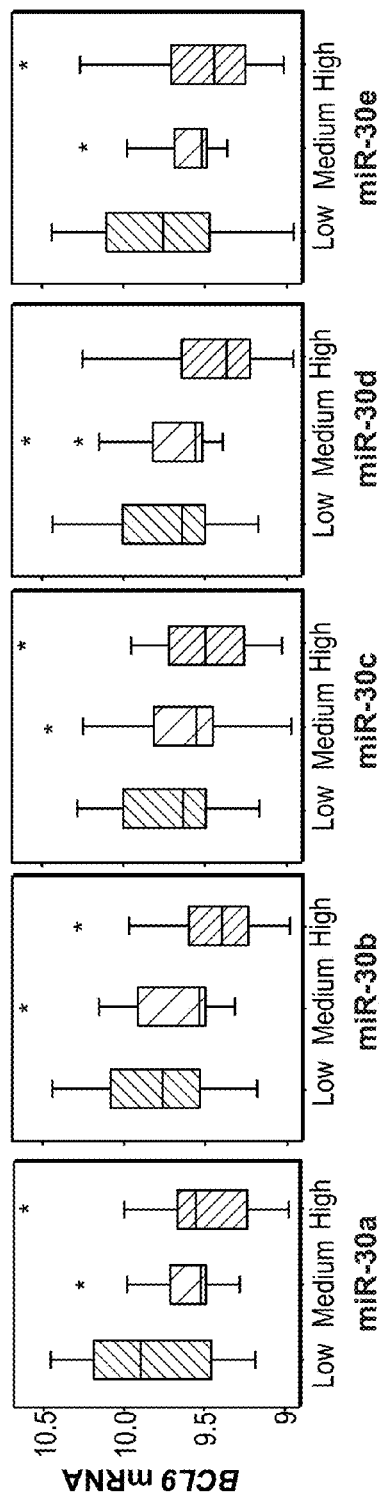

The invention provides methods and composition for treating hematologic malignancies by administering miR-30 RNA, and/or agents that increase amounts or activity of a miR-30 RNA, to a subject.

The inventors have discovered that miR-30-5p downregulation occurs as a result of an interaction between multiple myeloma (MM) cells and bone marrow stromal cells, which, in turn, enhances expression of BCL9, a transcriptional co-activator of the Wnt signaling pathway known to promote MM cell proliferation, survival, migration, drug resistance and formation of MM cancer stem cells. miR-30-5p as a therapeutic approach was further encouraged by the capacity of miR-30c and miR-30mix to reduce tumor burden and metastatic potential in vivo in three murine xenograft models of human MM without adversely affecting associated bone disease.

Agents that Increase miR-30 Levels or Activity

In general, any agent that increases levels or activity of a miR-30 RNA can be used in the methods described herein. Thus, by agent is meant any compound that mediates increased activity or levels of a miR-30 RNA in a cell, e.g., a plasma cell, of a subject with multiple myeloma. Suitable agents include, e.g., miR-30 RNA polynucleotides disclosed herein and viruses encoding the miR-30 polynucleotides.

miR-30 polynucleotides useful in the invention include the following:

```
                                            (SEQ ID NO: 1)
    has-miR-30a UGUAAACAUCCUCGACUGGAAG (SEQ ID NO: 2)
    has-miR-30b UGUAAACAUCCUACACUCAGCU (SEQ ID NO: 3)
    has-miR-30C UGUAAACAUCCUACACUCUCAGC (SEQ ID NO: 4)
    has-miR-30d UGUAAACAUCCCCGACUGGAAG (SEQ ID NO: 5)
    has-miR-30e UGUAAACAUCCUUGACUGAAG
```

The skilled artisan recognizes that miRNAs are transcribed as hairpin precursors and are then sequentially processed by the RNase III enzymes, Drosha and Dicer, to yield double-stranded intermediates bearing 2 nt, 3' overhanging ends. The duplexes are imperfectly paired and are subsequently generated into cytoplasmic protein-RNA complexes referred to as RNA-Induced Silencing Complexes (RISCs), which mediate RNA silencing. Each RISC comprises a single-stranded small RNA guide that is bound to a member of the Argonaute family of proteins. The miRNA and Argonaute protein act together to bind and silence respective target mRNAs. Perfectly complementary targets are efficiently silenced by the endonucleolytic cleavage activity of some Argonaute proteins, but the vast majority of predicted targets in animals are only partially paired and likely cannot be cleaved. Instead, they bind RISC using the "seed" of the miRNA, nucleotides 2-7, and are translationally repressed and/or degraded.

The terms "microRNA" or "miRNA" or "miR" are used interchangeably herein refer to endogenous RNA molecules, which act as gene silencers to regulate the expression of protein-coding genes at the post-transcriptional level. Endogenous microRNA are small RNAs naturally present in the genome which are capable of modulating the productive utilization of mRNA. The term artificial microRNA includes any type of RNA sequence, other than endogenous micro-RNA, which is capable of modulating the productive utilization of mRNA. MicroRNA sequences have been described in publications such as Lim, et al., Genes & Development, 17, p. 991-1008 (2003), Lim et al., Science 299, 1540 (2003), Lee and Ambros, Science, 294, 862 (2001), Lau et al., Science 294, 858-861 (2001), Lagos-Quintana et al., Current Biology, 12, 735-739 (2002), Lagos Quintana et al., Science 294, 853-857 (2001), and Lagos-Quintana et al., RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

During miRNA maturation in animals, the primary transcript is first processed to a stem-loop precursor and then the stem-loop is processed to yield a mature miRNA of about 22 nucleotides. These molecules can direct the cleavage of mRNA or they can interfere with productive translation of the mRNA, either of which results in reduced protein accumulation and hence the miRNAs are able to modulate gene expression and related cellular activities. miRNAs are important in development and differentiation, and thus the altered expression of miRNAs could be used to alter development and differentiation during tissue engineering and other applications. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways. Mimetics of miRNAs include, artificial miRNAs, and siRNAs are inefficient and are not effective for many small RNA sequences.

The term "pri-miRNA" refers to a precursor microRNA molecule having a microRNA sequence in the context of microRNA flanking sequences. A precursor microRNA, also referred to as large RNA precursors, are composed of any type of nucleic acid-based molecule capable of accommodating the microRNA flanking sequences and the microRNA sequence. Examples of precursor microRNAs and the individual components of the precursor (flanking sequences and microRNA sequence) are provided herein. The invention, however, is not limited to the examples provided. The invention is based, at least in part, on the discovery of an important component of precursor microRNAs, that is, the microRNA flanking sequences. The nucleotide sequence of the precursor and its components may vary widely. In one aspect a precursor microRNA molecule is an isolated nucleic acid; including microRNA flanking sequences and having a stem-loop structure with a microRNA sequence incorporated therein.

A precursor microRNA molecule may be processed in vivo or in vitro to produce a mature microRNA (miRNA). A precursor microRNA molecule is processed in a host cell by a ribonuclease enzyme or enzymes. One example of a ribonuclease enzyme which processes precursor microRNA molecules is the RNase II ribonuclease Dicer. The term "pre-miRNA" refers to the intermediate miRNA species from the processing of a pre-miRNA to a mature miRNA. Pre-miRNAs are produced from the processing of a pri-miRNA in the nucleus into a pre-miRNA. Pre-miRNAs undergo additional processing in the cytoplasm to form mature miRNA. Pre-miRNAs are approximately 70 nucleotides long, but can be less than 70 nucleotides or more than 70 nucleotides.

The terms "microRNA" or "miRNA" or "miR" are used interchangeably herein refer to endogenous RNA molecules, which act as gene silencers to regulate the expression of protein-coding genes at the post-transcriptional level. Endogenous microRNA are small RNAs naturally present in the genome which are capable of modulating the productive utilization of mRNA. The term artificial microRNA includes any type of RNA sequence, other than endogenous micro-RNA, which is capable of modulating the productive utilization of mRNA. MicroRNA sequences have been described in publications such as Lim, et al., Genes & Development, 17, p. 991-1008 (2003), Lim et al., Science 299, 1540 (2003), Lee and Ambros, Science, 294, 862 (2001), Lau et al., Science 294, 858-861 (2001), Lagos-Quintana et al., Current Biology, 12, 735-739 (2002), Lagos Quintana et al., Science 294, 853-857 (2001), and Lagos-Quintana et al., RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

During miRNA maturation in animals, the primary transcript is first processed to a stem-loop precursor and then the stem-loop is processed to yield a mature miRNA of about 22 nucleotides. These molecules can direct the cleavage of mRNA or they can interfere with productive translation of the mRNA, either of which results in reduced protein accumulation and hence the miRNAs are able to modulate gene expression and related cellular activities. miRNAs are important in development and differentiation, and thus the altered expression of miRNAs could be used to alter development and differentiation during tissue engineering and other applications. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways. Mimetics of miRNAs include, artificial miRNAs, and siRNAs are inefficient and are not effective for many small RNA sequences.

A precursor microRNA molecule may be processed in vivo or in vitro to produce a mature microRNA (miRNA). A precursor microRNA molecule is processed in a host cell by a ribonuclease enzyme or enzymes. One example of a ribonuclease enzyme which processes precursor microRNA molecules is the RNase II ribonuclease Dicer. The term "pre-miRNA" refers to the intermediate miRNA species from the processing of a pre-miRNA to a mature miRNA. Pre-miRNAs are produced from the processing of a pri-miRNA in the nucleus into a pre-miRNA. Pre-miRNAs undergo additional processing in the cytoplasm to form mature miRNA. Pre-miRNAs are approximately 70 nucleotides long, but can be less than 70 nucleotides or more than 70 nucleotides.

The term "miRNA" is used according to its ordinary and plain meaning and refers to a microRNA molecule found in eukaryotes that is involved in RNA-based gene regulation. See, e.g., Carrington et al., Science, 301:336-38, 2003, which is hereby incorporated by reference. The term will be used to refer to the single-stranded RNA molecule processed from a precursor. Individual miRNAs have been identified and sequenced in different organisms, and they have been given names. Names of miRNAs and their sequences are provided herein.

In some embodiments, short nucleic acid molecules function as miRNAs. The term "short" refers to a length of a single polynucleotide that is 150 nucleotides or fewer. In some embodiments the nucleic acid molecules are synthetic. The term "synthetic" means the nucleic acid molecule is isolated and not identical in sequence (the entire sequence) and/or chemical structure to a naturally-occurring nucleic acid molecule, such as an endogenous precursor miRNA molecule.

In some embodiments, nucleic acids do not have an entire sequence that is identical to a sequence of a naturally-occurring nucleic acid. In other embodiments, the nucleic acids encompass all or part of a naturally-occurring sequence. It is contemplated, however, that a synthetic nucleic acid administered to a cell may subsequently be modified or altered in the cell such that its structure or sequence is the same as non-synthetic or naturally occurring nucleic acid, such as a mature miRNA sequence.

For example, a synthetic nucleic acid may have a sequence that differs from the sequence of a precursor miRNA, but that sequence may be altered once in a cell to be the same as an endogenous, processed miRNA. The term "isolated" means that the nucleic acid molecules are separated from different (in terms of sequence or structure) and unwanted nucleic acid molecules such that a population of isolated nucleic acids is at least about 90% homogenous, and may be at least about 95, 96, 97, 98, 99, or 100% homogenous with respect to other polynucleotide molecules. In some embodiments, a nucleic acid is isolated by virtue of it having been synthesized in vitro separate from endogenous nucleic acids in a cell. It will be understood, however, that isolated nucleic acids may be subsequently mixed or pooled together.

A "synthetic nucleic acid" means that the nucleic acid does not have a chemical structure or sequence of a naturally occurring nucleic acid. Consequently, it will be understood that the term "synthetic miRNA" refers to a "synthetic nucleic acid" that functions in a cell or under physiological conditions as a naturally occurring miRNA.

In some embodiments the nucleic acid molecule(s) need not be "synthetic." In certain embodiments, a non-synthetic miRNA has the entire sequence and structure of a naturally occurring miRNA precursor or the mature miRNA. For example, non-synthetic miRNAs used in methods and compositions herein may not have one or more modified nucleotides or nucleotide analogs. In these embodiments, the non-synthetic miRNA may or may not be recombinantly produced. In particular embodiments, the nucleic acid is specifically a synthetic miRNA and not a non-synthetic miRNA (that is, not an miRNA that qualifies as "synthetic"); though in other embodiments, the invention specifically includes a non-synthetic miRNA and not a synthetic miRNA. Any embodiments discussed with respect to the use of synthetic miRNAs can be applied with respect to non-synthetic miRNAs, and vice versa.

The term "naturally occurring" refers to something found in an organism without any intervention by a person; it could refer to a naturally-occurring wildtype or mutant molecule. In some embodiments a synthetic miRNA molecule does not have the sequence of a naturally occurring miRNA molecule. In other embodiments, a synthetic miRNA molecule may have the sequence of a naturally occurring miRNA molecule, but the chemical structure of the molecule, particularly in the part unrelated specifically to the precise sequence (non-sequence chemical structure) differs from chemical structure of the naturally occurring miRNA molecule with that sequence. In some cases, the synthetic miRNA has both a sequence and non-sequence chemical structure that are not found in a naturally-occurring miRNA. Moreover, the sequence of the synthetic molecules will identify which miRNA is effectively being provided or inhibited; the endogenous miRNA will be referred to as the "corresponding miRNA."

Synthetic miRNA can include, e.g., RNA or RNA analogs. miRNA inhibitors may be DNA or RNA, or analogs thereof miRNA and miRNA inhibitors are collectively referred to as "synthetic nucleic acids."

Examples of modified nucleotides and/or nucleotides that can be used are those disclosed at http://mods.ma.albany.edu/home, which is maintained by the RNA Institute, College of Arts and Sciences, State University of New York at Albany, Albany, N.Y. In some embodiments, the RNA molecules include one or more of the following: 1-methyladenosine; $N^6$-methyladenosine; 2'-O-methyladenosine; $N^6$-isopentenyladenosine; $N^6$-(cis-hydroxyisopentenyl)adenosine; 2-methylthio-$N^6$-(cis-hydroxyisopentenyl) adenosine; $N^6$-glycinylcarbamoyladenosine; $N^6,N^6,2'$-O-trimethyladenosine; $N^6$-threonylcarbamoyladenosine; 2-methylthio-$N^6$-threonyl carbamoyladenosine; 2'-O-ribosyladenosine (phosphate); $N^6,N^6$-dimethyladenosine; $N^6,2'$-O-dimethyladenosine; $N^6,N^6,2'$-O-trimethyladenosine; 1,2'-O-dimethyladenosine; inosine; 1-methylinosine; 2'-O-methylinosine; 3-methylcytidine; 5-methylcytidine; 2'-O-methylcytidine; $N^4$-acetylcytidine; 5-formylcytidine; $N^4$-methylcytidine; 5-hydroxymethylcytidine; 5-formyl-2'-O-methylcytidine; 1-methylguanosine; $N^2$-methylguanosine; 7-methylguanosine; 2'-O-methylguanosine; $N^2,N^2$-dimethylguanosine; 2'-O-ribosylguanosine (phosphate); Wybutosine; peroxywybutosine; hydroxywybutosine; undermodified hydroxywybutosine; wyosine; $N^2$,7-dimethylguanosine; $N^2,N^2$,7-trimethylguanosine; queuosine; galactosyl-queuosine; mannosyl-queuosine; pseudouridine; dihydrouridine; 5-methyluridine; 2'-O-methyluridine; 5,2'-O-dimethyluridine; 1-methylpseudouridine; 2'-O-methylpseudouridine; 2-thiouridine; 5-methyl-2-thiouridine; 5-hydroxyuridine; 5-(carboxyhydroxymethyl)uridine; 5-(carboxyhydroxymethyl)uridine methyl ester; 5-methoxycarbonylmethyluridine; 5-methoxycarbonylmethyl-2'-O-methyluridine; 5-methoxycarbonylmethyl-2-thiouridine; 5-carbamoylmethyluridine; 5-carbamoylmethyl-2'-O-methyluridine; 5-carboxymethylaminomethyluridine; 3-methyluridine; 1-methyl-3-(3-amino-3-carboxypropyl) pseudouridine; 5-carboxymethyluridine; 3,2'-O-dimethyluridine; 5-methyldihydrouridine; 5-taurinomethyluridine; and/or 5-taurinomethyl-2-thiouridine.

In some embodiments, the miR-30 RNA is a synthetic miRNA having a length of between 15 and 130 residues, i.e., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 residues in length, or any range derivable therein.

In certain embodiments, synthetic miRNA have a) an "miRNA region" whose sequence from 5' to 3' is identical to a mature miRNA sequence, and b) a "complementary region" whose sequence from 5' to 3' is between 60% and 100% complementary to the miRNA sequence. In certain embodiments, these synthetic miRNA are also isolated, as defined above. The term "miRNA region" refers to a region on the synthetic miRNA that is at least 90% identical to the entire sequence of a mature, naturally occurring miRNA sequence. In certain embodiments, the miRNA region is or is at least 90, 91, 92, 93, 94, 95, 96, 97, 98, 99, 99.1, 99.2, 99.3, 99.4, 99.5, 99.6, 99.7, 99.8, 99.9 or 100% identical to the sequence of a naturally-occurring miRNA.

In some embodiments, a synthetic miRNA contains one or more design elements. These design elements include, but are not limited to: i) a replacement group for the phosphate or hydroxyl of the nucleotide at the 5' terminus of the complementary region; ii) one or more sugar modifications in the first or last 1 to 6 residues of the complementary region; or, iii) noncomplementarity between one or more nucleotides in the last 1 to 5 residues at the 3' end of the complementary region and the corresponding nucleotides of the miRNA region.

In certain embodiments, a synthetic miRNA has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group, an acetyl group, 2'O-Me (2'oxygen-methyl), DMTO (4,4'-dimethoxytrityl with oxygen), fluorescein, a thiol, or acridine, though other replacement groups are well known to those of skill in the art and can be used as well. This design element can also be used with an miRNA inhibitor.

Additional embodiments concern a synthetic miRNA having one or more sugar modifications in the first or last 1 to 6 residues of the complementary region (referred to as the "sugar replacement design"). In certain cases, there are one or more sugar modifications in the first 1, 2, 3, 4, 5, 6 or more residues of the complementary region, or any range derivable therein. In additional cases, there are one or more sugar modifications in the last 1, 2, 3, 4, 5, 6 or more residues of the complementary region, or any range derivable therein, have a sugar modification. It will be understood that the terms "first" and "last" are with respect to the order of residues from the 5' end to the 3' end of the region. In particular embodiments, the sugar modification is a 2'O-Me modification. In further embodiments, there are one or more sugar modifications in the first or last 2 to 4 residues of the complementary region or the first or last 4 to 6 residues of the complementary region. This design element can also be used with an miRNA inhibitor. Thus, an miRNA inhibitor can have this design element and/or a replacement group on the nucleotide at the 5' terminus, as discussed above.

Synthetic miRNA may have one or more of the replacement, sugar modification, or noncomplementarity designs. In certain cases, synthetic RNA molecules have two of them, while in others these molecules have all three designs in place.

In some embodiments, the agent is a mIR-30 RNA that hybridizes specifically to sequence motifs d \wt-1 (9129-9135 bp) and wt-2 (9880-9886 bp) in a 3'LTR of BCL9 mRNA.

In some embodiments, the miR-30 agent comprises the nucleotide sequence of one or more of a miR-30a, miR-30b, miR-30c, miR-30d, miR-30e, and/or or miR-30s RNA. If desired, the composition can be provided as a mix, or cocktail, of one or more miR-30 oligonucleotides, i.e., the composition can include miR-30a, miR-30b, miR-30c, miR-30d, miR-30e, and/or or miR-30s RNA.

Pharmaceutical Preparations

Pharmaceutical compositions comprise an effective amount an agent that increases miR-30 RNA levels dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one composition will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity (e.g., a purity sufficient for administering the composition to a human subject) standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The compositions may be contained in different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The composition may be formulated into a composition in a free base, neutral or salt form. Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further, the composition can be provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the composition is provided in a pharmaceutical lipid vehicle composition that includes an agent that increases miR-30 RNA levels and an aqueous solvent. As used herein, the term "lipid" is defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods described herein.

One of ordinary skill in the art would be familiar with the range of techniques that can be employed for dispersing a composition in a lipid vehicle. For example, the composition may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes. In specific embodiments, the composition is administered to an individual in a liposome.

The actual dosage amount of a composition administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary miR-30 Compositions and Formulations

In some embodiments, the compositions are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup or elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively, the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, compositions for delivering an agent that increases miR-30 RNA or activity are administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,753,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the active compound may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration may also include a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

The pharmaceutical compositions described herein find use in treating MM. Typically, the compositions can be used to treat Monoclonal Gammopathy of Undetermined Significance (MGUS), smoldering myeloma, asymptomatic MM, and symptomatic MM, ranging from newly diagnosed to late stage relapsed/refractory.

The miR-30 compositions can be combined with other treatment strategies, i.e., autologous stem cell transplantation and allogeneic effector cell transplantation, to develop an effective treatment strategy based on the stage of myeloma being treated (see, e.g., Multiple Myeloma Research Foundation, Multiple Myeloma: Stem Cell Transplantation 1-30 (2004); U.S. Pat. Nos. 6,143,292, and 5,928,639, Igarashi, et al. Blood 2004, 104(1): 170-177, Maloney, et al. 2003, Blood, 102(9): 3447-3454, Badros, et al. 2002, J Clin Oncol., 20:1295-1303, Tricot, et al. 1996, Blood, 87(3):1196-1198; the contents of which are incorporated herein by reference).

The effectiveness of miR-30 multiple myeloma treatment can be assessed using methods known in the art. The staging system most widely used since 1975 has been the Durie-Salmon system, in which the clinical stage of disease (Stage I, II, or III) is based on four measurements (see, e.g., Durie and Salmon, 1975, Cancer, 36:842-854). These four measurements are: (1) levels of monoclonal (M) protein (also known as paraprotein) in the serum and/or the urine; (2) the number of lytic bone lesions; (3) hemoglobin values; and, (4) serum calcium levels. These three stages can be further divided according to renal function, classified as A (relatively normal renal function, serum creatinine value <2.0 mg/dL) and B (abnormal renal function, creatinine value.greatoreq.2.0 mg/dL). A new, simpler alternative is the International Staging System (ISS) (see, e.g., Greipp et al., 2003, "Development of an international prognostic index (IPI) for myeloma: report of the international myeloma working group", The Hematology). The ISS is based on the assessment of two blood test results, beta$_2$-microglobulin ($\beta_2$-M) and albumin, which separates patients into three prognostic groups irrespective of type of therapy. Administration of the pharmaceutical compositions at selected dosage ranges and routes typically elicits a beneficial response as defined by the European Group for Blood and Marrow transplantation (EBMT) in Table 1, below (taken from U.S. Pat. No. 8,632,772). Table 1 lists the EBMT criteria for response:

| EBMT/IBMTR/ABMTR[1] Criteria for Response | |
| --- | --- |
| Complete Response | No M-protein detected in serum or urine by immunofixation for a minimum of 6 weeks and fewer than 5% plasma cells in bone marrow >50% |
| Partial Response | reduction in serum M-protein level and/or 90% reduction in urine free light chain excretion or reduction to <200 mg/24 hrs for 6 weeks[2] |
| Minimal Response | 25-49% reduction in serum M-protein level and/or 50-89% reduction in urine free light chain excretion which still exceeds 200 mg/24 hrs for 6 weeks[3] |
| No Change | Not meeting the criteria or either minimal response or progressive disease |
| Plateau | No evidence of continuing myeloma-related organ or tissue damage, <25% change in M-protein levels and light chain excretion for 3 months |
| Progressive Disease | Myeloma-related organ or tissue damage continuing despite therapy or its reappearance in plateau phase, >25% increase in serum M-protein level (>5 g/L) and/or >25% increase in urine M-protein level (>200 mg/24 hrs) and/or >25% increase in bone marrow plasma cells (at least 10% in absolute terms)[2] |
| Relapse | Reappearance of disease in patients previously in complete response, including detection of paraprotein by immunofixation |

[1]EBMT: European Group for Blood and Marrow transplantation; IBMTR: International Bone Marrow Transplant Registry; ABMTR: Autologous Blood and Marrow Transplant Registry.

Additional criteria that can be used to measure the outcome of a treatment include "near complete response" and "very good partial response". A "near complete response" is defined as the criteria for a "complete response" (CR), but with a positive immunofixation test. A "very good partial response" is defined as a greater than 90% decrease in M protein (see, e.g., Multiple Myeloma Research Foundation, Multiple Myeloma: Treatment Overview 9 (2005)).

The degree to which administration of the composition elicits a response in an individual clinically manifesting at least one symptom associated with MM, depends in part, on the severity of disease, e.g., Stage I, II, or III, and in part, on whether the patient is newly diagnosed or has late stage refractory MM. Thus, in some embodiments, administration of the pharmaceutical composition elicits a complete response.

In some embodiments, administration of the pharmaceutical composition elicits a very good partial response or a partial response. In other embodiments, administration of the pharmaceutical composition elicits a minimal response. In other embodiments, administration of the pharmaceutical composition prevents the disease from progressing, resulting in a response classified as "no change" or "plateau" by the EBMT.

Combination Treatments

An agent that increases miR-30 RNA levels can be administered along with an additional therapy or therapies for treating multiple myeloma. For example, in some embodiments, an agent that increases levels or activity of miR-30 RNA is administered following the administration of a second therapeutic agent for treating multiple myeloma. Administration of each member of the combination can be sequential or simultaneous. For example, an agent that increases levels or activity of miR-30 RNA can be administered approximately 0 to 60 days after the administration of another therapeutic agent.

The therapeutic agents can be administered in any manner found appropriate by a clinician and are typically provided in generally accepted efficacious dose ranges, such as those described in the Physician Desk Reference, 56th Ed. (2002), Publisher Medical Economics, New Jersey. In other embodiments, a standard dose escalation can be performed to identify the maximum tolerated dose (MTD) (see, e.g., Richardson, et al. 2002, Blood, 100(9):3063-3067, the content of which is incorporated herein by reference).

In some embodiments, doses less than the generally accepted efficacious dose of a therapeutic agent can be used. For example, in various embodiments, the composition comprises a dosage that is less than about 10% to 75% of the generally accepted efficacious dose range. In some embodiments, at least about 10% or less of the generally accepted efficacious dose range is used, at least about 15% or less, at least about 25%, at least about 30% or less, at least about 40% or less, at least about 50% or less, at least about 60% or less, at least about 75% or less, and at least about 90%.

The therapeutic agents administered in a combination treatments can be administered in the same or different routes, i.e., each or both can be administered orally, intravenously, systemically by injection intramuscularly, subcutaneously, intrathecally or intraperitoneally.

Examples of therapeutic agents that can be used in the compositions described herein include, but are not limited to, dexamethasone, thalidomide, melphalan, prednisone, doxorubicin, doxorubicin HCL liposome injection, bortezomib, lenalidomide, and/or combinations thereof.

Accordingly, in some embodiments, two pharmaceutical compositions are provided: a first comprising a therapeutically effective amount of an agent that increases levels or activity of miR-30 RNA and a second comprising a therapeutically effective amount of lenalidomide.

In some embodiments, two pharmaceutical compositions are provided: a first comprising a therapeutically effective amount of an agent that increases levels or activityy of miR-30 and a second comprising a therapeutically effective amount of bortezomib. In some embodiments, at least two pharmaceutical compositions are provided: a first comprising a therapeutically effective amount of an agent that increases levels or activity of miR-30 RNA and a second comprising a therapeutically effective amount of lenalidomide and a therapeutically effective amount of bortezomib. In some embodiments, lenalidomide and bortezomib are provided separately, such that a total of three pharmaceutical compositions are provided: a first comprising an agent that increases levels or activity of miR-30 RNA, a second comprising lenalidomide, and a third comprising bortezomib. In some embodiments, at least two pharmaceutical compositions are provided: a first comprising a therapeutically effective amount of an agent that increases levels or activity of miR-30 RNA, and a second comprising a therapeutically effective amount of lenalidomide and dexamethasone. In some embodiments, lenalidomide and dexamethasone are provided separately, such that a total of three pharmaceutical compositions are provided: a first comprising an agent that increases levels or activity of miR-30 RNA, a second comprising lenalidomide, and a third comprising dexamethasone. In some embodiments at least two pharmaceutical compositions are provided: for example, a first comprising a therapeutically effective amount of an agent that increases levels or activity of miR-30 RNA, and a second comprising a therapeutically effective amount of bortezomib and dexamethasone. In some embodiments, bortezomib and dexamethasone are provided separately, such that a total of three pharmaceutical compositions are provided: a first comprising an agent that increases levels or activity of miR-30 RNA, and a second comprising bortezomib, and a third comprising dexamethasone.

In some embodiments, at least two pharmaceutical compositions are provided: a first comprising a therapeutically effective amount of an agent that increases levels or activity of miR-30 RNA, and a second comprising therapeutically effective amount of lenalidomide, bortezomib, and dexamethasone. In some embodiments, lenalidomide, bortezomib, and dexamethasone are provided separately. Provided that the agents retain their efficacy, compositions comprising other combinations can be prepared, depending in part, on dosage, route of administration, and whether the agents are provided in a solid, semi-solid or liquid form. For example, a total of three compositions can be made: a first comprising a therapeutically effective amount of an agent that increases levels or activity of miR-30 RNA, a second comprising dexamethasone, and a third comprising lenalidomide and bortezomib.

In some embodiments, at least two pharmaceutical compositions are provided: a first comprising a therapeutically effective amount of an agent that increases levels or activityy of miR-30 RNA, and a second comprising a therapeutically effective amount of bortezomib and optionally can comprise one or more of the following agents: thalidomide, dexamethasone, melphalan, doxorubicin, doxorubicin HCl liposome injection, and/or prednisone. Provided that the agents retain their efficacy, compositions comprising various combinations of thalidomide, dexamethasone, melphalan, doxorubicin, doxorubicin HCl liposome injection, and prednisone can be prepared depending in part, on dosage, route of administration, and whether the agents are provided in a solid, semi-solid or liquid form.

Diagnosing Multiple Myeloma

The invention additionally provides a method for diagnosing myeloma or a related condition, e.g., a precursor to myeloma, multiple myeloma cancers which produce light chains of kappa-type and/or light chains of lambda-type; aggressive multiple myeloma; refractory multiple myeloma, and drug resistant multiple myeloma. The method includes detecting in a sample obtained from a subject an miR-30 RNA. A lower level of RNA relative to a corresponding control sample from a subject known not to have multiple myelomaindicates the subject has multiple myeloma.

The diagnostic methods are performed using methods known in the art for analyzing nucleic acid sequences. The term "diagnosis of a disease" encompasses screening for a disease, diagnosing a diseases, detecting the presence or a severity of a disease, prognosis of a diseases, monitoring of disease progression and/or treatment efficacy and/or relapse of a disease, disorder or condition, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations.

In some embodiments, the diagnostic methods are performed with a sample isolated from a subject having, predisposed to, or suspected of having any one or more of the above types of multiple myeloma (including without limitation its precursor diseases).

In some embodiments, the sample is a cell or tissue or a body fluid sample. In at least some embodiments, the subject invention therefore also relates to diagnostic methods and or assays for diagnosis a disease optionally in a biological sample taken from a subject (patient), which is optionally some type of body fluid or secretion including but not limited to seminal plasma, blood, serum, urine, prostatic fluid, seminal fluid, semen, the external secretions of the skin, respiratory, intestinal, and genitourinary tracts, tears, cerebrospinal fluid, sputum, saliva, milk, peritoneal fluid, pleural fluid, cyst fluid, broncho alveolar lavage, lavage of the reproductive system and/or lavage of any other part of the body or system in the body, and stool or a tissue sample. The term may also optionally encompass samples of in vivo cell culture constituents. The sample can optionally be diluted with a suitable eluant before contacting the sample to an antibody and/or performing any other diagnostic assay In some embodiments, the diagnostic methods include the detection of at least one of miR-30 RNA a fragment or a variant or a homolog thereof, by employing a nucleic acid-based technology. In some embodiments, the LNA (locked nuclear acid)-based assay is, e.g., a PCR, Real-Time PCR, LCR, Self-Sustained Synthetic Reaction, Q-Beta Replicase, Cycling Probe Reaction, Branched DNA, RFLP analysis, DGGE/TGGE, Single-Strand Conformation Polymorphism, Dideoxy Fingerprinting, Microarrays, Fluorescence In Situ Hybridization or Comparative Genomic Hybridization.

The invention additionally includes a kit that comprises markers and reagents for detecting levels of miR-30 RNA the changes by employing a LNA-based technology. In some embodiments, the kit includes at least one nucleotide probe or primer. In at least some embodiments, the kit comprises at least one primer pair capable of selectively hybridizing to a nucleic acid sequence according to the teaching of the present invention. In at least some embodiments of the present invention, the kit comprises at least one oligonucleotide capable of selectively hybridizing to a nucleic acid sequence according to the teaching of the present invention.

Optionally diagnosing comprises screening for multiple myeloma in a subject, detecting a presence or a severity of multiple myeloma in a subject, distinguishing multiple myeloma from other diseases, providing prognosis of multiple myeloma, monitoring progression or relapse of multiple myeloma, in a subject, assessment of treatment efficacy or relapse of multiple myeloma, in a subject, selecting a therapy and a treatment for multiple myeloma, in a subject, optimization of a given therapy for multiple myeloma, in a subject, monitoring the treatment of multiple myeloma, in a subject, predicting the suitability of a therapy for specific patients or subpopulations, determining the appropriate dosing of a therapeutic product in patients or subpopulations. Optionally, determining the expression level comprises applying an IHC (immunohistochemistry) assay or a gene expression assay to a tissue of the subject.

As used herein, the use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The invention will be further illustrated in the following non-limiting examples.

Example 1

General Materials and Methods

Sequences of miR Nucleic Acids and Other Polynucleotide Sequences

The sequences of the oligonoucleotides used herein are provided in Table 2.

| Primers | Sequences (5'->3') |
|---|---|
| pmiR-Bcl9-wt-1F | CGCGTTGCCATCGGTCATGTGTTGCACCGTTCTCTGTATGTTTACGTCCTTTGG ACTGGCTTCTCGGATCCA (SEQ ID NO: 6) |
| pmiR-Bcl9-wt-1R | AGCTTGGATCCGAGAAGCCAGTCCAAAGGACGTAAACATACAGAGAACGGT GCAACACATGACCGATGGCAA (SEQ ID NO: 7) |
| pmiR-Bcl9-mut-1F | CGCGTTGCCATCGGTCATGTGTTGCACCGTTCTCTGTAGTCCTTTGGACTGGC TTCTCGGATCCA (SEQ ID NO: 8) |
| pmiR-Bcl9-mut-1R | AGCTGGATCCGAGAAGCCAGTCCAAAGGACTACAGAGAACGGTGCAACACA TGACCGATGGCAA (SEQ ID NO: 9) |
| pmiR-Bcl9-wt-2F | CGCGTGTCTTTGGGGCAAGAGGAGAACAGGAATGCTGGGCTGTTTACTTTAG GTGGAGAATCCATGGATCCA (SEQ ID NO: 10) |
| pmiR-Bcl9-wt-2R | AGCTTGGATCCATGGATTCTCCACCTAAAGTAAACAGCCCAGCATTCCTGTTC TCCTCTTGCCCCAAAGACA (SEQ ID NO: 11) |
| pmiR-Bcl9-mut-2F | CGCGTGTCTTTGGGGCAAGAGGAGAACAGGAATGCTGGGCTTTAGGTGGAGA ATCCATGGATCCA (SEQ ID NO: 12) |
| pmiR-Bcl9-mut-2R | AGCTTGGATCCATGGATTCTCCACCTAAAGCCCAGCATTCCTGTTCTCCTCTT GCCCCAAAGACA (SEQ ID NO: 13) |
| CD44 F | TTTGCATTGCAGTCAACAGTC (SEQ ID NO: 14) |
| CD44 R | TGAGTCCACTTGGCTTTCTGT (SEQ ID NO: 15) |
| Axin2 F | CGGAAACTGTTGACAGTGGAT (SEQ ID NO: 16) |
| Axin2 R | GGTGCAAAGACATAGCCAGAA (SEQ ID NO: 17) |
| GAPDH F | GCACCGTCAAGGCTGAGAAC (SEQ ID NO: 18) |
| GAPDH R | TGGTGAAGACGCCAGTGGA (SEQ ID NO: 19) |
| Scramble | AAGGCAAGCUGACCCUGAAGU (SEQ ID NO: 20) |
| Anti-miR-30a | CUUCCAGUCGAGGAUGUUUACA (SEQ ID NO: 21) |
| Anti-miR-30b | AGCUGAGUGUAGGAUGUUUACA (SEQ ID NO: 22) |
| Anti-miR-30c | GCUGAGAGUGUAGGAUGUUUACA (SEQ ID NO: 23) |
| Anti-miR-30d | CUUCCAGUCGGGGAUGUUUACA (SEQ ID NO: 24) |
| Anti-miR-30e | CUUCCAGUCAAGGAUGUUUACA (SEQ ID NO: 25) |
| cel-miR-67 | UCACAACCUCCUAGAAAGAGUAGA (SEQ ID NO: 26) |
| has-miR-30a | UGUAAACAUCCUCGACUGGAAG (SEQ ID NO: 27) |
| has-miR-30b | UGUAAACAUCCUACACUCAGCU (SEQ ID NO: 28) |
| has-miR-30c | UGUAAACAUCCUACACUCUCAGC (SEQ ID NO: 29) |
| has-miR-30d | UGUAAACAUCCCCGACUGGAAG (SEQ ID NO: 30) |
| has-miR-30e | UGUAAACAUCCUUGACUGGAAG (SEQ ID NO: 31) |

MiRs Microarray Analysis

Total RNA was isolated using a Trizol reagent (Invitrogen). MiRs profiling was performed using a Taqman miRs expression array (Applied Biosystem). Gene expression from dataset GSE27306 was normalized by RMA (Robust Multiarray Averaging) method and using refseq CDF annotation files. Processed miRs expression was used. Both linear "pearson" and non-linear one "spearman" correlation co-efficient were calculated, and a correlation test was applied to test the difference between these two independent correlation coefficients.

All samples were divided based on miR-30 members' expression into three equal-size groups (low, medium, high), followed by side-by-side boxplots of BCL9 expression, and then an ANOVA test of BCL9 expression between the three groups. A P-value was generated by the ANOVA test.

Cell Proliferation, Apoptosis, Invasion, and Migration Assays.

Cell proliferation was assessed by [$^3$H] thymidine uptake as described (1). For apoptosis, cells were stained with Annexin-V-Fluos (Boehringer, Mannheim, Germany). Stained cells were analyzed by flow cytometry, and data were analyzed by use of CellQuest (Becton-Dickinson, Sunnyvale, Calif.). Cell invasion and migration assays were done as described (2).

Soft Agar Colony Formation Assay.

Cells were added to 0.35% low-melting-temperature agarose (Seaplaque) containing DMEM culture medium as described above, and transferred at a density of $0.5 \times 10^6$ cells/plate to 6 cm cell culture plates previously lined with 0.5% agar DMEM culture medium. After 15 days, the colonies were stained with 0.005% Crystal violet and counted.

SP Staining and Macro Sphere Formation Assays.

Hoechst 33342 SP staining was performed as described (3). SP cells (1000 cells/mL) were sorted and cultured in serum-free stem cell medium with DMEM-F12 (BioWhittaker) supplemented with B27 (1:50, Invitrogen), 20 ng/mL EGF (BD Biosciences), 0.4% BSA (Sigma), and 4 µg/mL insulin (Sigma). Spheres per well (1000 sorted SP cells/well) were counted after 3 days of culture.

Statistical Analysis.

Statistical significance of differences between groups was analyzed by unpaired Student's t test, and $p<0.05$ was considered to be statistically significant.

Microarray Data Processing, GSE Analysis and Statistical Analysis.

RNA from triplicate samples of H929 treated with sh-BCL9 or miR30mix and corresponding controls, scrambled shRNA and miR-67 respectively was isolated for gene expression profiling analyses. Total RNA was hybridized to Affymetrix Human U133 Plus 2.0 arrays. The rma function of the R affy Bioconductor package was used for signal summarization and background correction. The R limma Bioconductor package (5) was used to identify significantly up- and down-regulated probe sets. Probe sets with a >2-fold change after shBCL9 treatment and an adjusted P-value <0.05 were used to create shBCL9 gene sets. These signatures were then used for GSEA in the $\log_2$-converted miR-30 data set. Microarray data has been deposited to the Gene Expression Omnibus (http://www.ncbi.nlm.nih.gov/geo) and comply with MIAME annotation standards. GEO accession number: GSE50422.

Statistical significance of differences observed in miR-30c or miR-30s groups versus control V-GFP group was determined using the Student t test, and was achieved when P value <0.05. Survival of V-miR-30c and V-GFP mice survival was evaluated by Kaplan-Meier Survival Curve Analysis, with the log-rank statistic. All analyses were completed by the software SPSS11.0, and $p<0.05$ was considered statistically significant.

Mouse Xenograft Models of Tumor Burden and Metastasis.

$5 \times 10^6$ H929 MM cells stable transduced with V-miR-30 and V-GFP were injected subcutaneously (s.c.) or intravenously (i.v.) into hairless SCID Crl: SHO-Prkdc$^{scid}$Hr$^{hr}$ mice (STRAIN CODE 474, Charles River), as previously described (7). All experiments involving animals were approved by DFCI Institutional Animal Care and Use Committee. For s.c. injected mice, each animal was injected in flanks, one side with V-GFP H929 cells and the other side with V-GFP H929 cells. Tumor development was measured every 3 days from first appearance, and tumor volume was calculated as Volume=(Length×Width$^2$×3.1415926)/6. Animals were euthanized when tumors reached 2 cm$^3$. For i.v. injected mice, survival was evaluated from the first day of tumor injection until death. Hind limb paralysis and tumor burden were used as an end point in the disseminated disease model, and GFP positive tumor image was captured by LAS-4000 Luminescent Imager Analyzer (Fujifilm). To assess in vivo cell proliferation, apoptosis activity, and expression of downstream target genes of miR-30s, GFP-positive tumor samples were excised from the murine xenograft models for IHC analysis, as in previous studies (7).

Micro-Computed Tomography.

Micro-computed topographic (µCT) imaging was performed on the L4-L6 vertebrae of the intact spine of a subset of mice using a high-resolution desktop imaging system (µCT40, Scanco Medical AG, Bruttiselllen, Switzerland). Scans were acquired using a 12 µm$^3$ isotropic voxel size, 70 kVp peak x-ray tube potential, and 200 ms integration time. Cortical and trabecular bone micro architecture was quantified in the 5$^{th}$ lumbar vertebral body in a region beginning 120 µm below the cranial growth plate and ending 120 µm above the caudal growth plate. To assess cortical lesions, we determined the cortical bone volume (Ct.BV) and total volume (Ct.TV) of the ventral face of the vertebral body. Cortical void fraction (%) was calculated as 1−(Ct.BV/Ct.TV)*100 and represents the percent of the ventral face that was void of bone. Trabecular bone volume fraction (Tb.BV/Tb.TV, %) was measured in the region of interest. In NOD/SCID mice not transplanted with myeloma cells, µCT was performed in one mouse treated with vehicle and one mouse treated with miR-30c after 10 days of treatment. In NOD/SCID mice transplanted with myeloma cells, µCT was performed in two selected mice (showing spine involvement by whole body imaging) for each experimental group at day 21 of treatment.

Example 2

MiR-30s is the Only Predicted miR Binding to the 3'UTR of BCL9 mRNA

Figure 2C:
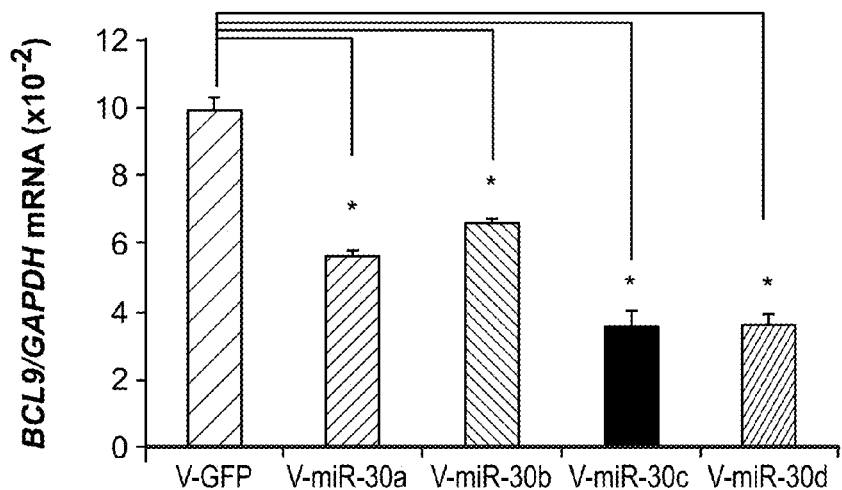

We investigated whether BCL9 mRNA expression is regulated by miRs. By searching databases TargetScan, PicTar, miRDB, and microCosm, we found that the 3'UTR of BCL9 mRNA contains two sequence motifs designated wt-1 (9129-9135 bp) and wt-2 (9880-9886 bp), which perfectly match with the "seed" sequence of the miR-30s family members (FIG. 2A).

Example 3

MiR-30s are Downregulated in MM Cells, and their Expression is Inversely Related with BCL9 Expression Expression profiling data from 78 MM patient samples showed that the levels of each miR-30 family member (miR-30a/b/c/d/e) were variable, and that 60% ($^{45}/_{78}$) of samples expressed low levels of miR-30s compared with nine normal PCs (FIG. 1A).

We next asked whether low levels of miR-30s were associated with high BCL9 mRNA expression levels, and vice versa using Q-RT-PCR analysis. A total of six normal PCs (N1-N6) and six patient MM cells (T1-T6) were examined in parallel for expression of miR-30s and BCL9 mRNA. We observed that normal PCs with undetectable levels of BCL9 mRNA display high levels of miR-30s expression, while patient MM cells with variable levels of BCL9 mRNA were almost devoid of miR-30s expression. This inverse relation was also detected in MM cell lines (FIG. 1C). For example, the H929 cell line that expresses relatively low levels of miR-30s showed high levels of BCL9 mRNA expression while the MM1 S cell line that expresses high levels of miR-30s showed relatively low levels of BCL9 mRNA expression.

Although miR-30s members are located at three different chromosomal regions: 1p34.2 (miR-30e and miR-30c-1), 6q13 (miR-30c-2 and miR-30a) and 8q24.22 (miR-30b and miR-30d), they all have similar expression patterns among different MM patient samples (FIG. 1A). This suggests they share a similar regulatory network that is independent of chromosomal copy number alterations. Indeed, miR-30c, the only member with two copies in the human genome, has the most abundant expression levels in normal PCs and shows the lowest levels of expression in MM patient samples, which frequently have chromosomal 1p34 and 6q13 deletions.

Figure 1E:
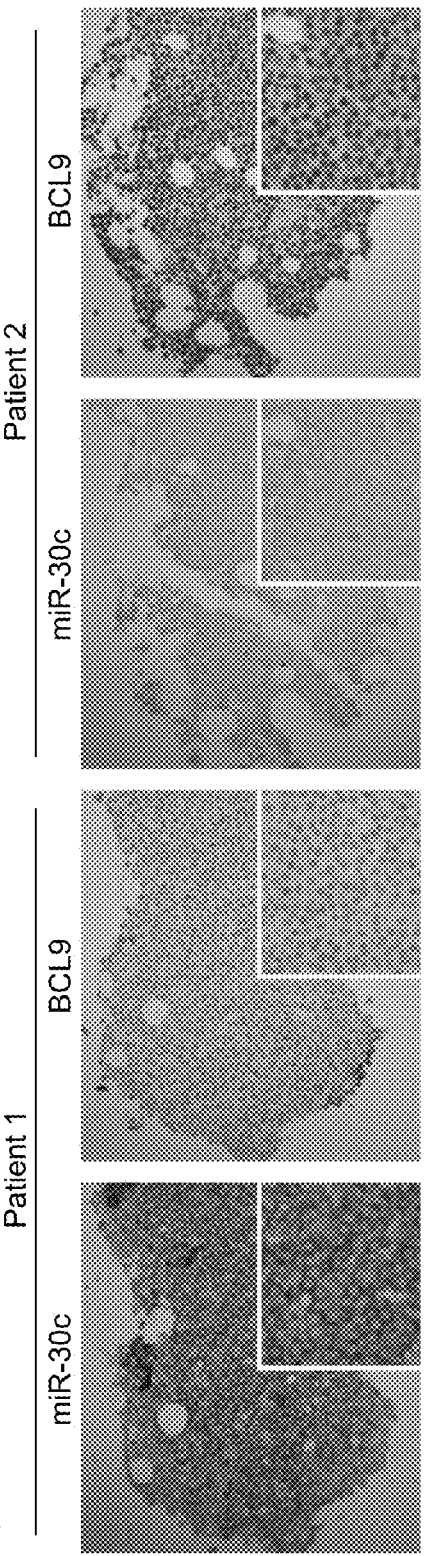

To further investigate the relation between BCL9 mRNA and miR-30s RNA levels, we analyzed published data set GSE17306, for which information for both mRNA and miR expression in MM patient samples is available. We found that BCL9 mRNA is highly expressed in late stage MM patient samples, and that its expression inversely associated with expression of miR-30a (also known as miR-30a-5p), miR-30b, miR-30c, miR-30d and miR-30e (also known as miR-30e-5p) ($p<0.05$) (FIG. 1D), but not with miR-30a-3p and miR-30e-3p, two miRs functionally unrelated to the miR-30s family ($p>0.05$, data not shown). In addition, we examined the relation between miR-30s and BCL9 protein levels on BM biopsies. Since miR-30c showed the most significant changes, (FIG. 1D), we selected this family member for this and further studies. MiR-LNA in situ hybridization (ISH) of miR-30c and IHC staining of BCL9 protein on 6 BM biopsies from MM patients also showed an inverse association between miR-30s expression and BCL9 protein levels (FIG. 1E).

Example 4

BCL9 mRNA is a Direct Target of miR-30s

In order to establish a functional relationship between miR-30s and BCL9 mRNA regulation, we first transduced individual pre-miR-30s into HEK293T cells using lentiviral vectors expressing GFP as a marker. Cells transduced with vector alone (V-GFP) were used as a control.

Figure 2D:
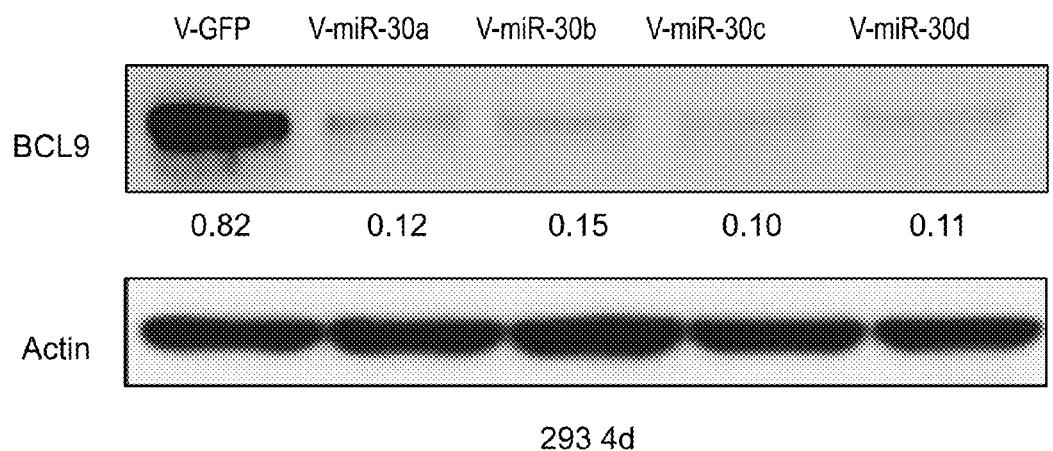

Ectopic expression of each pre-miR-30s member (FIG. 2B) was associated with down regulated expression of BCL9 mRNA and protein levels, as evaluated by Q-RT-PCR (FIG. 2C) and immunoblot analysis (FIG. 2D).

Figure 2E:
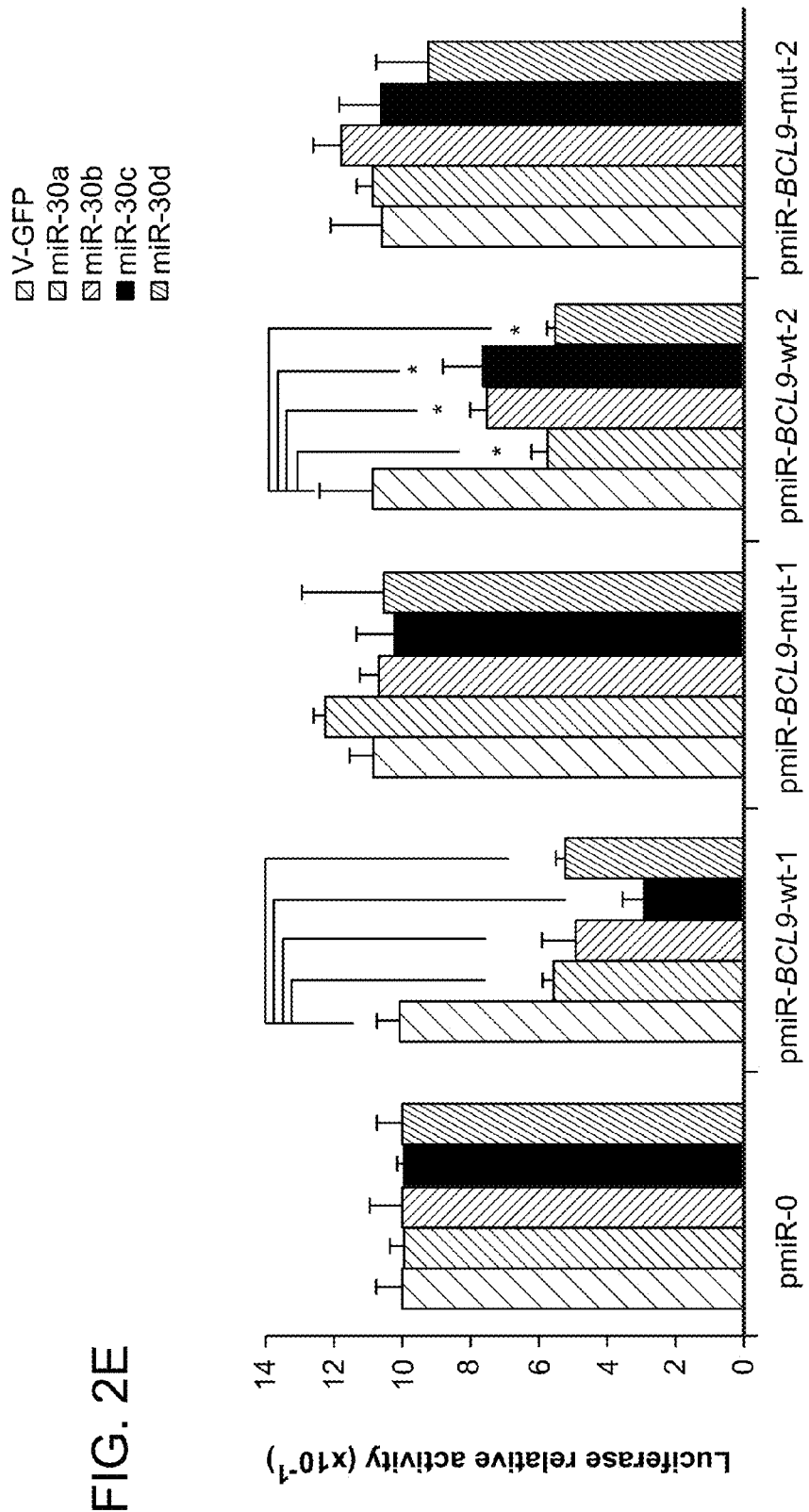

To further demonstrate that miR-30s directly regulates expression of BCL9 mRNA through binding to the 3'UTR, two wild type- (pmiR-BCL9-30-wt-1 and pmiR-BCL9-30-wt-2) and two mutant- (pmiR-BCL9-30-Mut-1 and pmiR-BCL9-30-Mut-2) (Table 2). BCL9-3'UTR reporter vectors were co-transfected into HEK293T cells, together with each individual V-miR-30s member or V-GFP. Luciferase activity of wild type constructs, but not mutant, was significantly decreased with each V-miR-30s compared to V-GFP (FIG. 2E). This confirmed the specificity of the interaction between miR-30s and BCL9-3'UTR mRNA.

Example 5

MiR-30s Regulates BCL9 mRNA Expression in MM Cells

We next investigated whether BCL9 mRNA expression is regulated by miR-30s in MM cells using both gain- and loss-of function studies. For gain-of-function studies we used H929 cells that express the lowest levels of miR-30s among the MM cell lines examined (FIG. 1C).

Figure 3A:
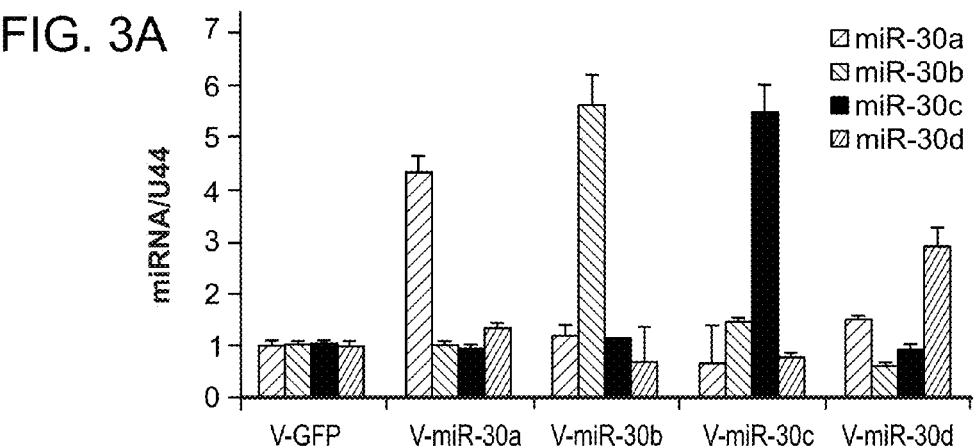
FIGS. 3A-G show that miR-30s inhibits BCL9 and Wnt target gene expression in multiple myeloma.

We first induced ectopic expression of individual V-miR-30s family members in H929 cells using lentiviral infection. After flow sorting of GFP positive cells, levels of miR-30s were verified by Q-RT-PCR (FIG. 3A) and then used in subsequent experiments.

Figure 3B:
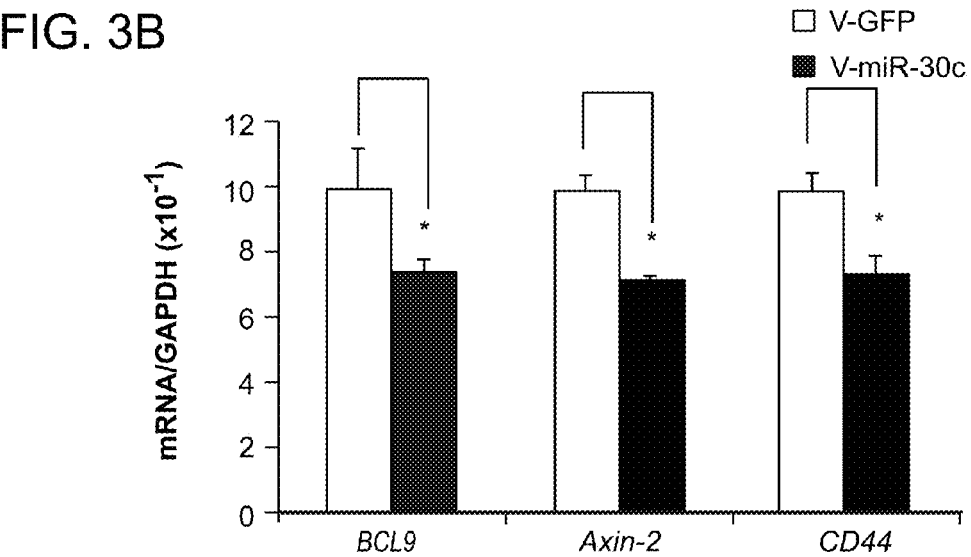
Figure 3C:
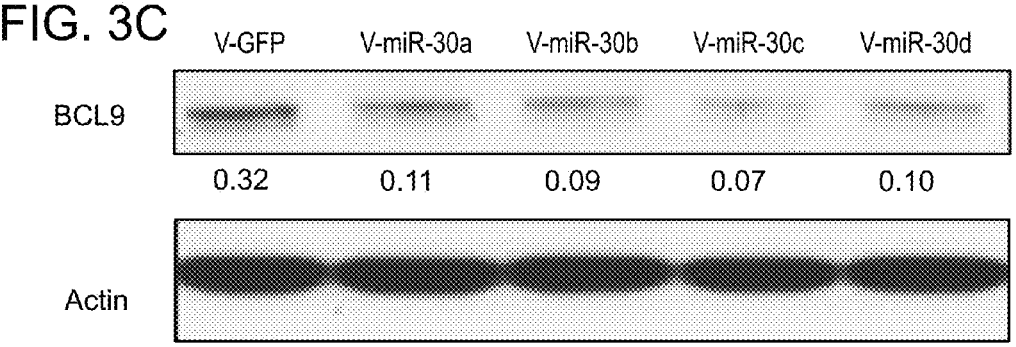
Figure 3E:
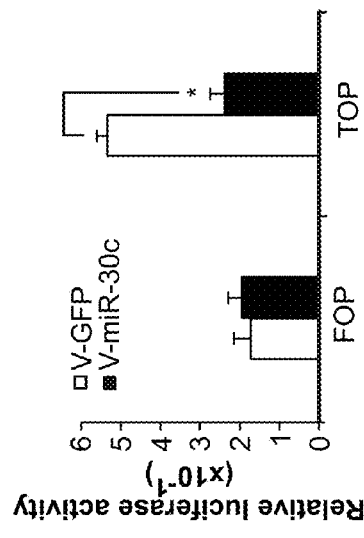

As shown in HEK293T cells (FIG. 2B, C), ectopic expression of miR-30c in MM cells was also associated with a significant reduction in the expression of BCL9 mRNA (FIG. 3B). Ectopic expression of miR-30s was also associated with a reduction in the expression of BCL9 protein, as evaluated by immunoblot (FIG. 3C) and IF (FIG. 3D) studies. Consistent with the role of BCL9 as a transcriptional co-activator of Wnt signaling pathway, ectopic expression of miR-30c was also associated with reduced expression of "bonafide" Wnt pathway downstream targets CD44 and Axin2 (FIG. 3B) as well as Wnt reporter FOP/TOP activity (FIG. 3E).

We next focused on evaluating the effect of the miR-30s family member miR-30c and validated its effect on BCL9 down regulation in other MM cell lines using immunoblot. Wild type TOP reporter activity was inhibited in V-miR-30c stable H929 cells compared with V-GFP stable H929 cells, while the mutant FOP activity was not changed (FIG. 3E).

Figure 3F:
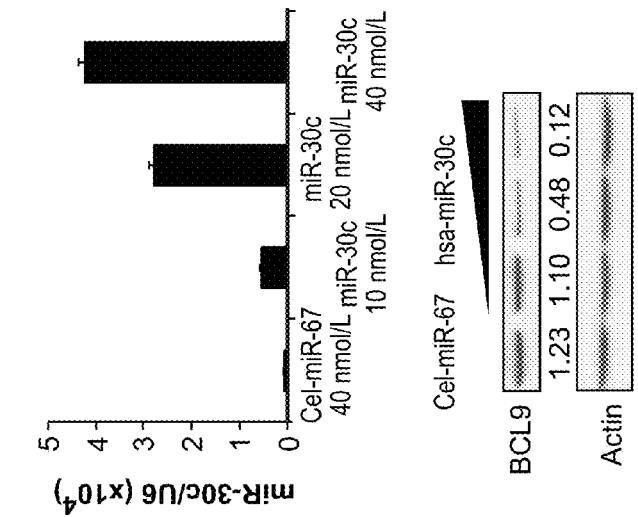
Figure 3D:
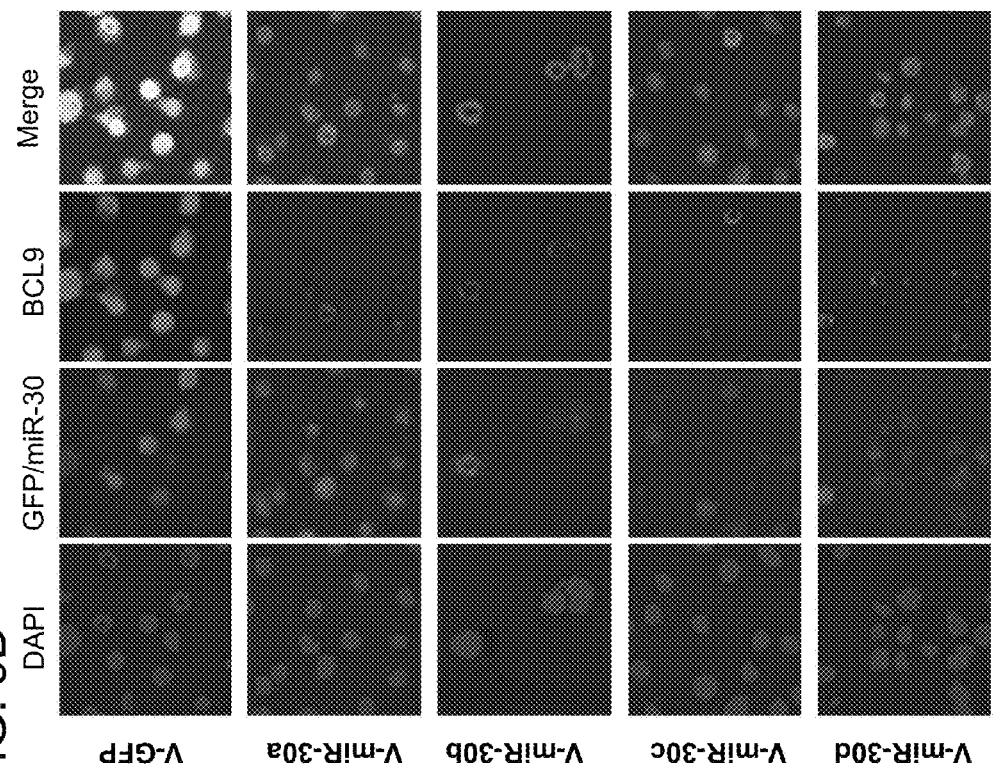

To exclude the possibility that the observed changes in BCL9 expression may be due to non specific and/or secondary effects of stable transfection of V-miR-30c, we also performed transient transfection with increasing amounts of mature miR-30c into RPMI8226 cells, using cel-miR-67 as a control (FIG. 3F).

To confirm transfection efficiency, cells were collected 72 hours after transfection, and miR-30c expression levels were checked by Q-RT-PCR (FIG. 3F, top). We found an inverse association between downregulation of BCL9 protein expression and increasing amounts of transfected mature miR-30c (FIG. 3F, bottom).

Figure 3G:
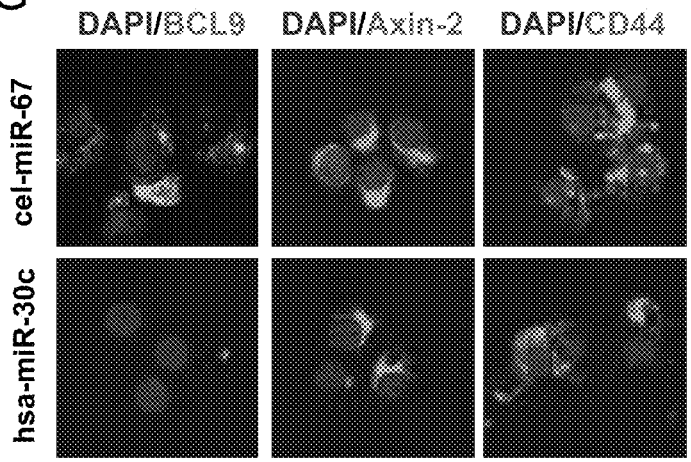

In order to verify miR-30's potential for therapy in MM patients, CD138+ primary cells (n=3) were transfected with 40 pmol of mature miR-30c or same amount of cel-miR-67 as control. Expression of BCL9, CD44 and Axin2 were downregulated as evaluated by IF in all three patient samples. One representative case is shown in FIG. 3G, top. Furthermore, MM cell proliferation was dramatically inhibited by miR-30c (FIG. 3G, bottom).

For loss-of-function studies we used the MM1S cell line, which expresses relatively high levels of miR-30s and relatively low levels of BCL9 mRNA. MM1S cells were transfected with a pool of 2'O-me anti-miR-30a/b/c/d/e cocktail (anti-miR-30mix) or scrambled oligonucleotides as a control. Q-RT-PCR analysis revealed a significant reduction of all members of miR-30s in cells treated with individual anti-miR-30s compared with cells transfected with scrambled oligonucleotides. Levels of BCL9 mRNA and protein were increased in 2'O-me anti-miR-30 treated cells compared with cells transfected with scrambled nucleotides. Furthermore, expression of the Wnt downstream targets Axin-2 and CD44 was upregulated, as was Wnt reporter activity, in MM1S cells treated with anti-miR-30mix, but not with scrambled oligonucleotides.

Example 6

Figure 4A:
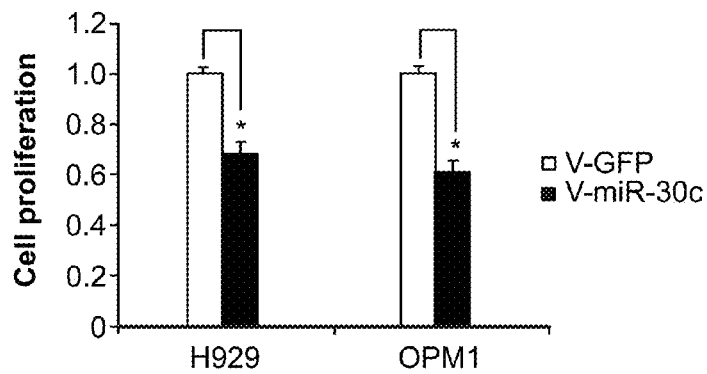
FIGS. 4A-D show that miR-30c inhibits cell proliferation, invasion, and migration, and induces apoptosis of multiple myeloma.
Figure 4B:
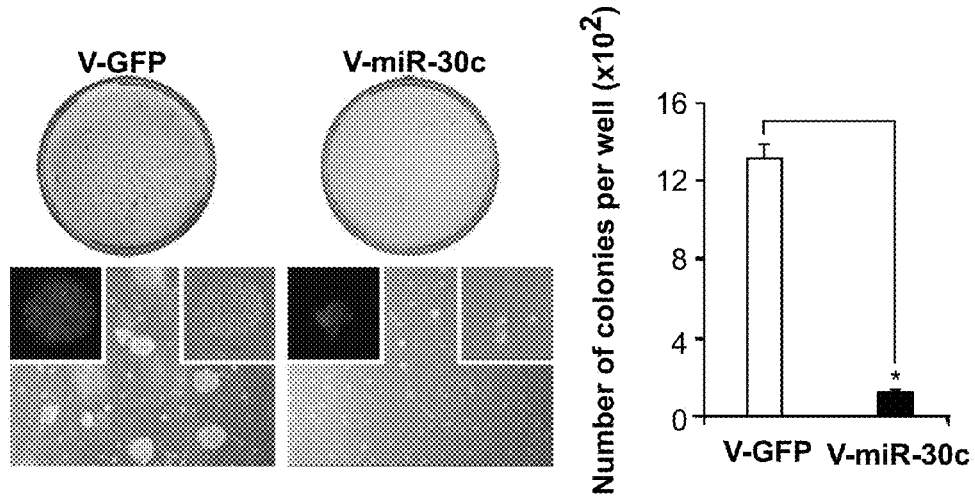
Figure 4C:
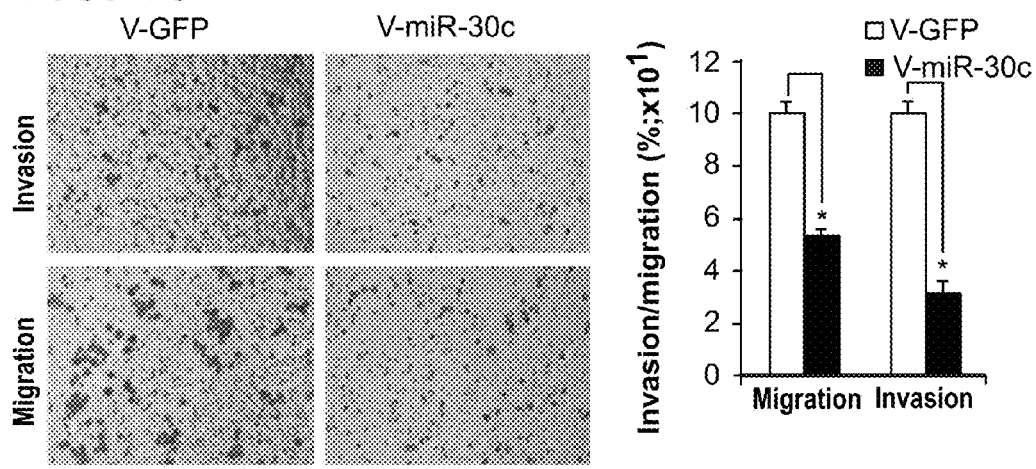
Figure 4D:
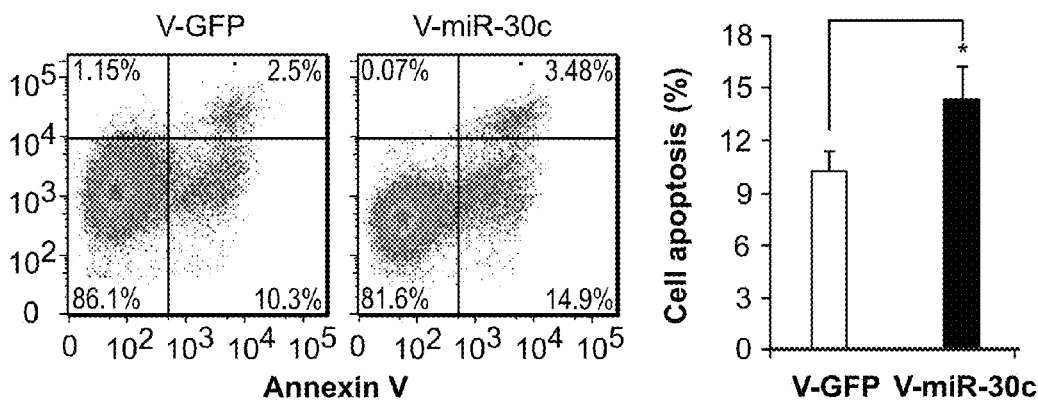
Figure 5A:
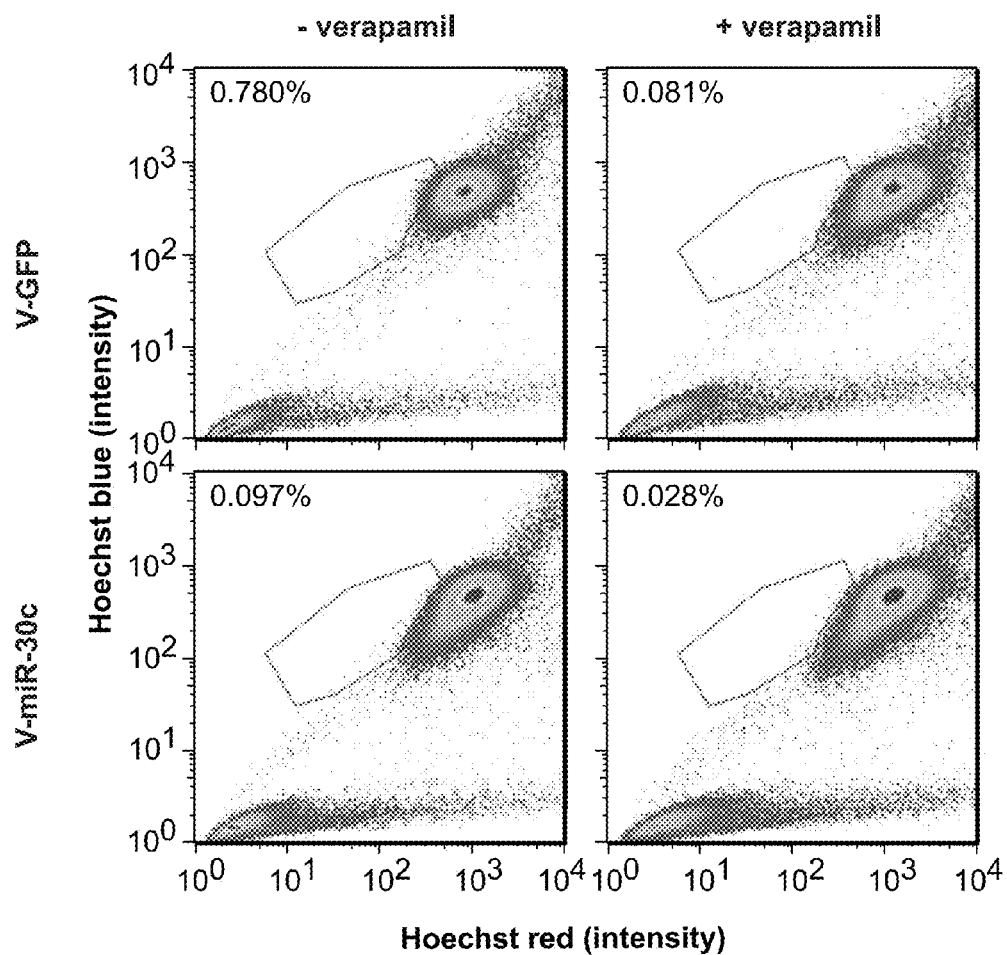
Figure 5B:
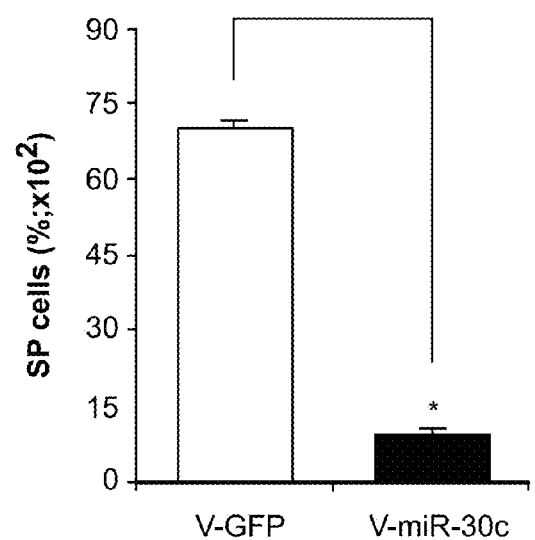
Figure 5C:
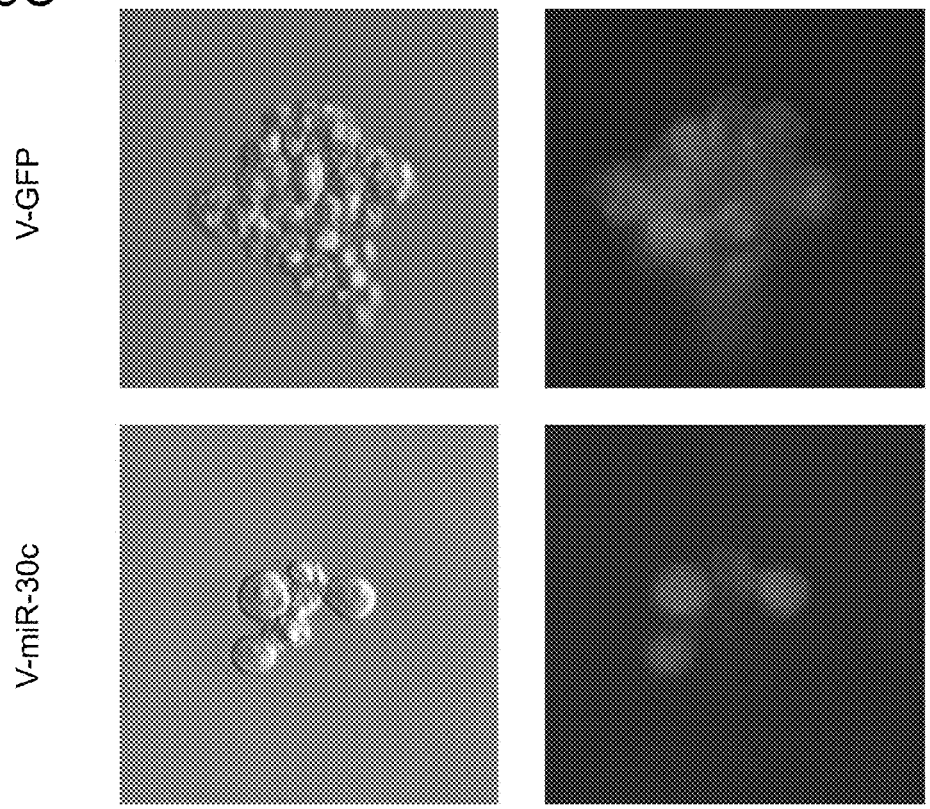
Figure 5D:
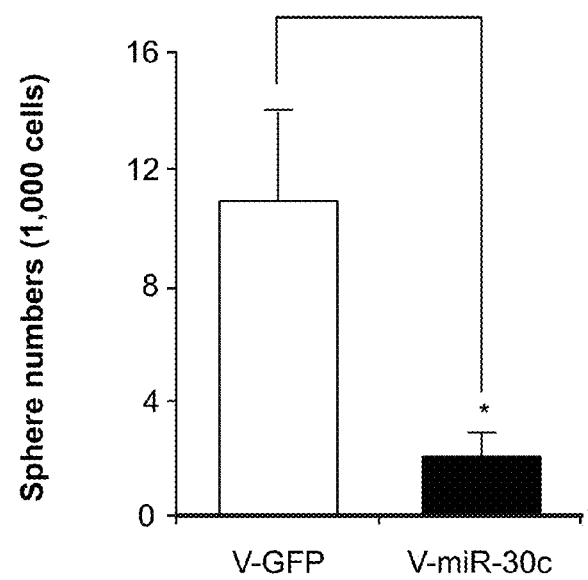

MiR-30c Inhibits MM Cell Proliferation, Invasion, Migration and Induces Apoptosis We examined whether miR-30s can mimic the functional consequences of BCL9 deregulation in multiple myeloma using the miR-30c family member. Based on the results shown in FIGS. 1D and 3, we focused on miR-30c. A consistent pattern emerged whereby H929 and OPM1 cells overexpressing miR-30c (V-miR-30c), but not control cells (V-GFP), showed significantly reduced proliferation (FIG. 4A), colony formation (FIG. 4B), invasion, and migration (FIG. 4C). In addition, we found that miR-30c induces a modest increase in apoptosis, from 10.1±1.1% in H929 cells expressing GFP (V-GFP) to 14.2±1.9% in H929 cells expressing miR-30c (V-miR-30c) (n=3, p<0.05) (FIG. 4D). Taken together, these data demonstrate that miR-30c specifically disrupts a series of physiologic processes regulated by the Wnt/BCL9/β-catenin transcriptional complex, and highlighting the potential therapeutic role of miR-30c in MM.

Example 7

MiR-30c Inhibits Multiple Myeloma Cancer Stem Cell Formation

We next investigated whether miR-30c is involved in regulating behavior of cancer stem cells (CSCs) in multiple myeloma (FIG. 5). Functional Hoechst22234 staining assay was employed to define the SP in V-miR-30c stably infected cells, and V-GFP cells were used as a control (FIG. 5A). The stem cell SP was significantly reduced from 0.698%±0.04% in H929 V-GFP cells to 0.068%±0.05% in H929 cells expressing V-miR-30c (n=3, p<0.05) (FIG. 5B).

Moreover, in experiments using stem cell medium to culture sorted SP cells (FIG. 5C), the sphere numbers (FIG. 5D) and size of spheres as evaluated by cell number per sphere (FIG. 5E) were significantly decreased in H929 V-miR-30c SP compared with H929 V-GFP control CSCs. These results highlight the potential role of miR-30c in blocking Wnt signaling pathway in CSC, further confirming the relevance of this pathway for target drug discovery in multiple myeloma.

Example 8

MiR-30c Restores Drug Sensitivity in Bone Marrow Stromal Cell-Induced Drug Resistance of Multiple Myeloma Bone marrow stem cells (BMSC) promote migration, homing, proliferation, survival, and drug resistance in multiple myeloma. The relatively high levels of miR-30s in MM cell lines compared with patient MM cells (FIGS. 1B and 1C) prompted us to next investigate the possible role of BMSCs in regulating miR-30s expression in MM cells. GFP-labeled H929 cells were co-cultured with HS-5 dsRed stable BMSCs. After 48 h of co-culture, GFP-positive H929 cells were flow sorted and total RNA was isolated for Q-RT-PCR analysis.

Co-culture with HS-5 dsRed downregulates expression of miR-30s in H929 cells, associated with enhanced expression of BCL9 mRNA and the Wnt downstream targets Axin-2 and CD44, but not of GAPDH, a non Wnt target gene used as a control.

Reasoning that CD44 is a downstream target of Wnt/β-catenin/BCL9 transcriptional complex, and that miR-30c downregulates expression of CD44 in MM cells (FIG. 3B), and that CD44 is a functional component of cell adhesion-mediated drug resistance (CAM-DR), we investigated the possible role of miR-30s in MM drug resistance in the context of a bone marrow (BM) microenvironment. After ectopic overexpression of miR-30c or miR-30a/b/c/d/e cocktail (miR-30mix) or a negative control (cel-miR-67) in H929 cells, we co-cultured these cells alone or in the presence of HS-5 cells for 48 h and treated them with 200 nM dexamethasone.

Interestingly, we found that both miR-30c and miR-30mix can resensitize the H929 cells to dexamethasone treatment, with the miR-30mix apparently being more effective than miR-30c. Overall, these findings indicate that expression of miR-30s in MM cells can be modulated by the BM microenvironment and further support its therapeutic usefulness to overcome CAM-DR.

Example 9

MiR-30c Inhibits Tumor Progression in Murine Xenograft Models of Human MM

To further explore the therapeutic potential of miR-30c, we next examined its capacity to suppress tumor growth and metastatic potential in vivo using two established murine xenograft models of human multiple myeloma. In the first model (i.e., subcutaneous), H929 V-GFP control and H929 V-miR-30c stably transduced cells were injected subcutaneously into opposite flanks of SCID mice. Tumor volume was evaluated over time up to day 25, when mice were sacrificed and whole body imaging was performed. As shown in FIG. 6A (top and bottom) tumor growth was significantly decreased in mice injected with H929 V-miR-30c as compared with H929 V-GFP control cells. In the second model (i.e. intravascular), H929 V-GFP control or H929 V-miR-30c stably transduced cells were injected by tail vein into SCID mice. Survival, tumor burden and spreading were assessed (FIG. 6B). Tumor involvement was observed in the intestine, spine, and skull, which was similar in V-miR-30c and V-GFP control group (122.5±33.0 days vs. 162.2±21.7 days, n=6, p=0.03) (FIG. 6B, top panel).

Figure 6D:
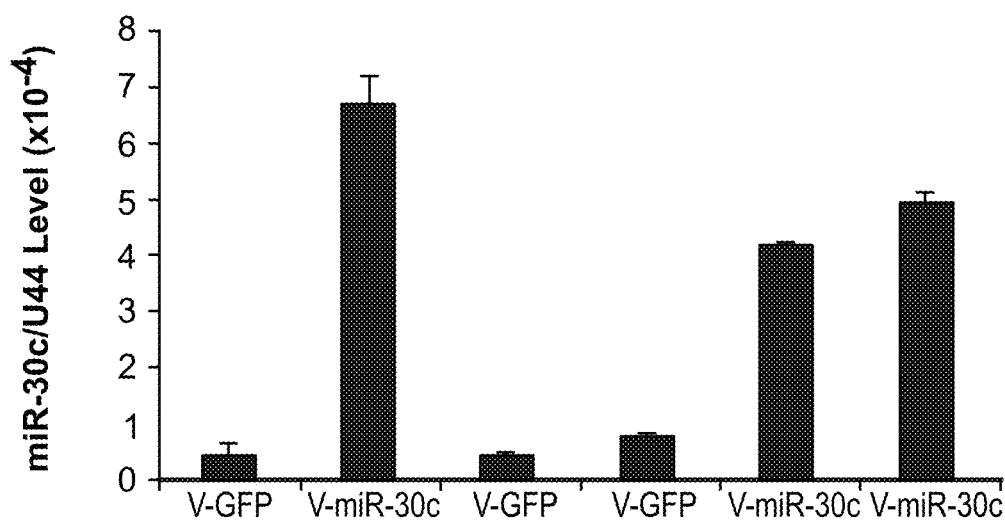
Figure 6D:
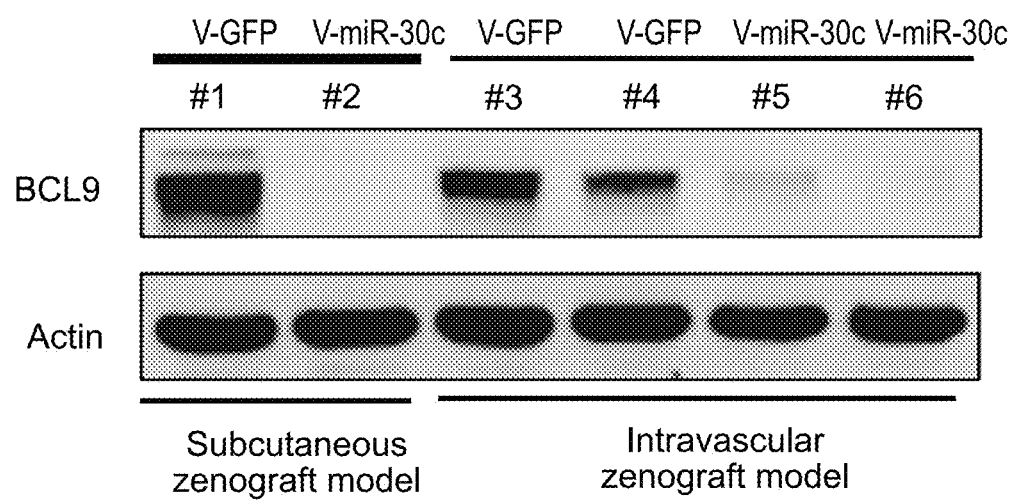

However, tumor burden was decreased and survival time significantly increased in mice injected with H929 V-miR-30c compared with H929 V-GFP control cells (FIG. 6B, bottom). In agreement with in vitro studies, tumors developing in mice injected with stable V-miR-30c H929 cells showed decreased expression levels of BCL9, Ki-67, CD44 and Axin2 proteins, as well as increased levels of Caspase 3 expression compared with V-GFP control tumors evidenced by IHC analysis (FIG. 6C). The miR-30c overexpression and downregulation of BCL9 in GFP-positive harvested tumors was further verified by Q-RT-PCR (FIG. 6C, upper panel) and immunoblot analyses (FIG. 6D, lower panel). Interestingly, BCL6, which is a target of miR-30 in diffuse large B-cell lymphomas, was not identified as a target in multiple myeloma.

We next addressed whether intraperitoneal delivery of miR-30s could inhibit MM tumor growth in vivo. We used miR-30s premixed with RNA-LANCErII, which is a mixture of neutral lipid, non-ionic detergent, and oil, to determine whether lipid nanoparticles could deliver miR-30s in to H929 MM cells, and if there was preferential delivery and inhibition of BCL9 expression among individual members of the miR30s family.

Figure 7A:
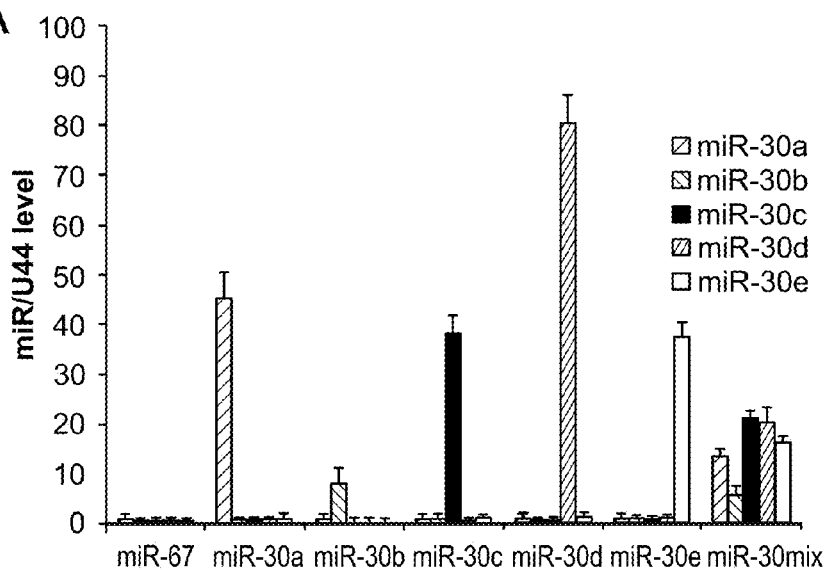
FIGS. 7A-G show miR-30s treatment decreases tumor burden in MM1S-Luc-Neo bearing mice.
Figure 7B:
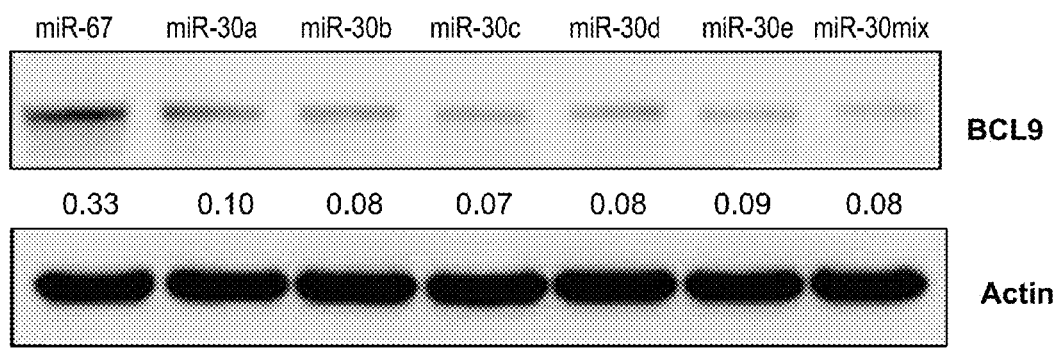

Q-RT-PCR analysis revealed that all miR-30 members were taken up by the cells, although to different extents, when added to the medium individually or as a miR-30a/b/c/d/e equimolar cocktail (miR-30mix) (FIG. 7A). In addition, all individual miR-30 members or the cocktail decreased expression of BCL9 to a similar extent, evaluated by immunoblot analysis (FIG. 7B).

Figure 7C:
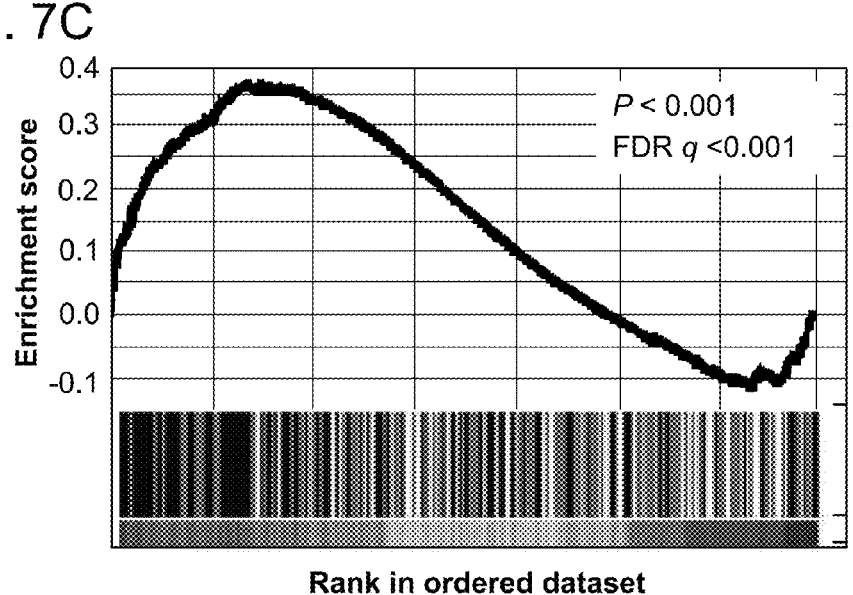

Reasoning that treatment with a cocktail mixture containing lower amounts of each individual member could be better tolerated by the mice, we performed this in vivo experiment with an miR-30mix. Therefore, we first investigated the specificity of miR-30mix treatment in inhibiting expression of Wnt/β-catenin/BCL9 transcriptional targets by performing comparative genome-wide expression analyses (FIG. 7C). We generated triplicate gene expression profiling data sets from H929 cells treated with miR-30mix or Cel-miR-67 (control) as well as from H929 cells lentivirally transduced with previously validated shRNA hairpins against BCL9 (sh-BCL9) or scrambled sequences (control) (9) using Affimetrix oligonucleotides microarrays. Gene set enrichment analysis (GSEA) revealed a statistically significant correlation between the genes downregulated by miR-30mix and by sh-BCL9 (family-wise error (FWER) p-value <0.001; false discovery rate (FDR) q-value <0.001), documenting the specificity of miR-30mix in blocking expression of Wnt/β-catenin/BCL9 transcriptional targets (FIG. 7C).

Figure 7D:
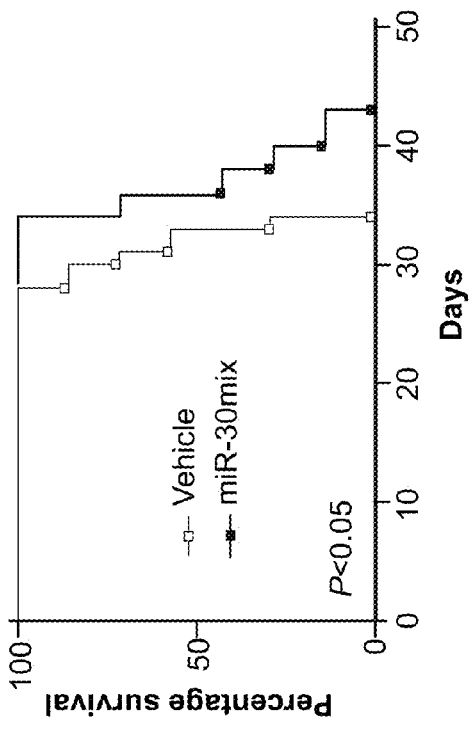
Figure 7E:
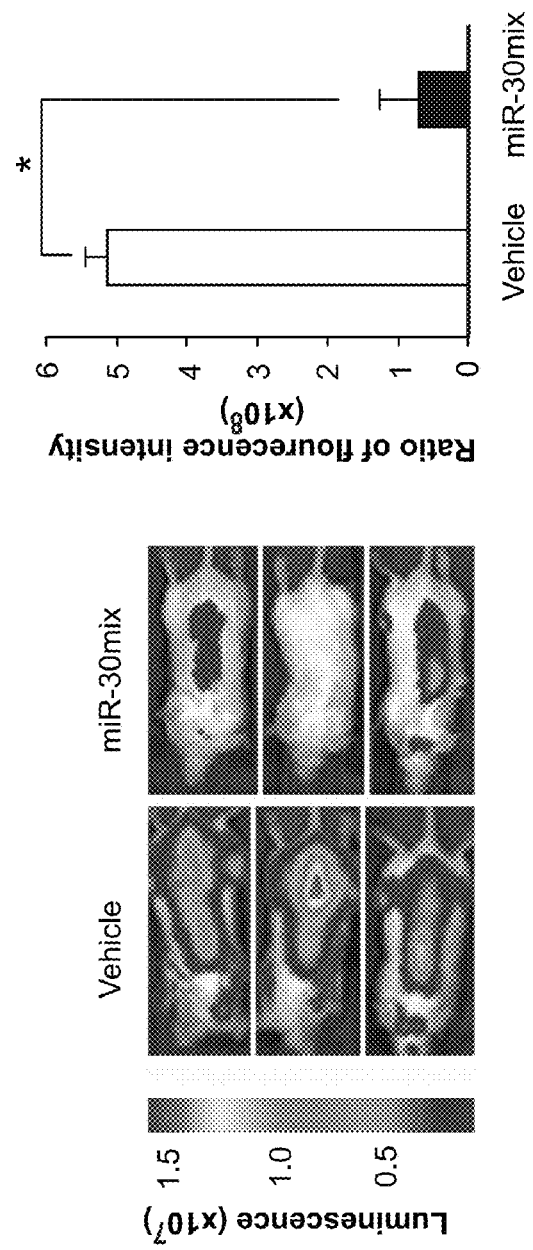
Figure 7F:
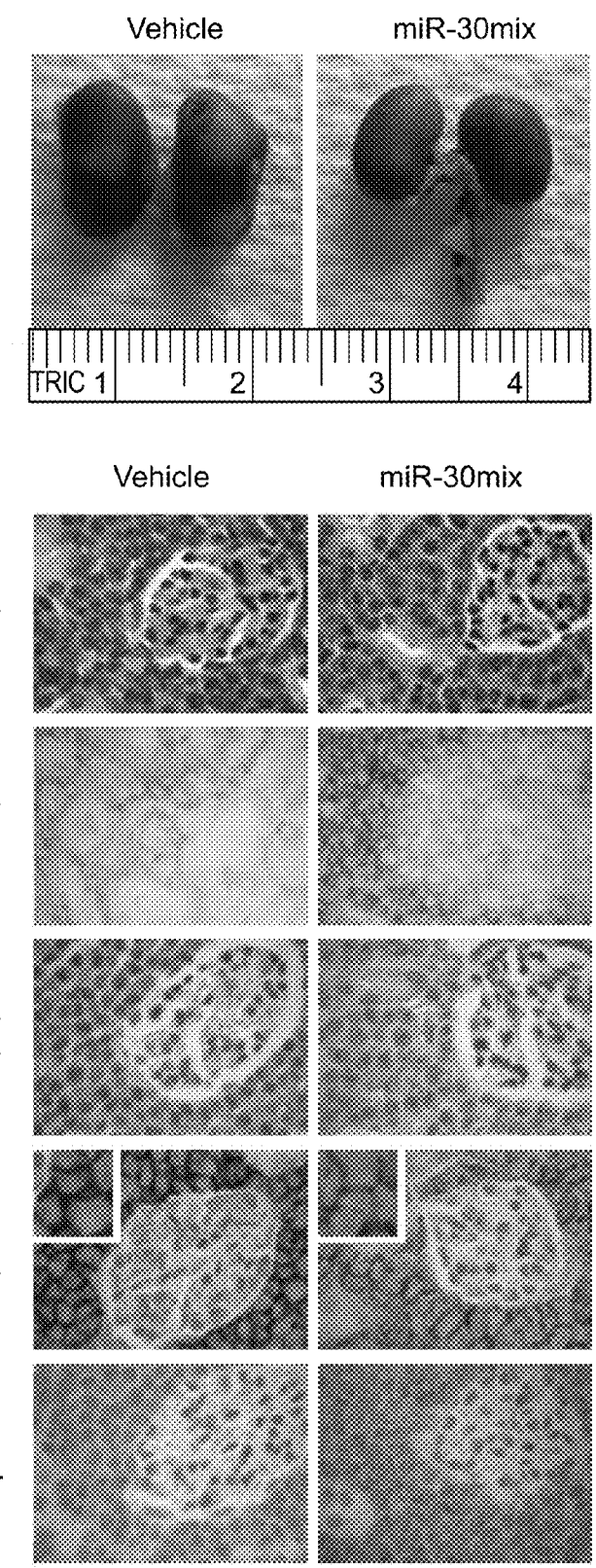
Figure 7G:
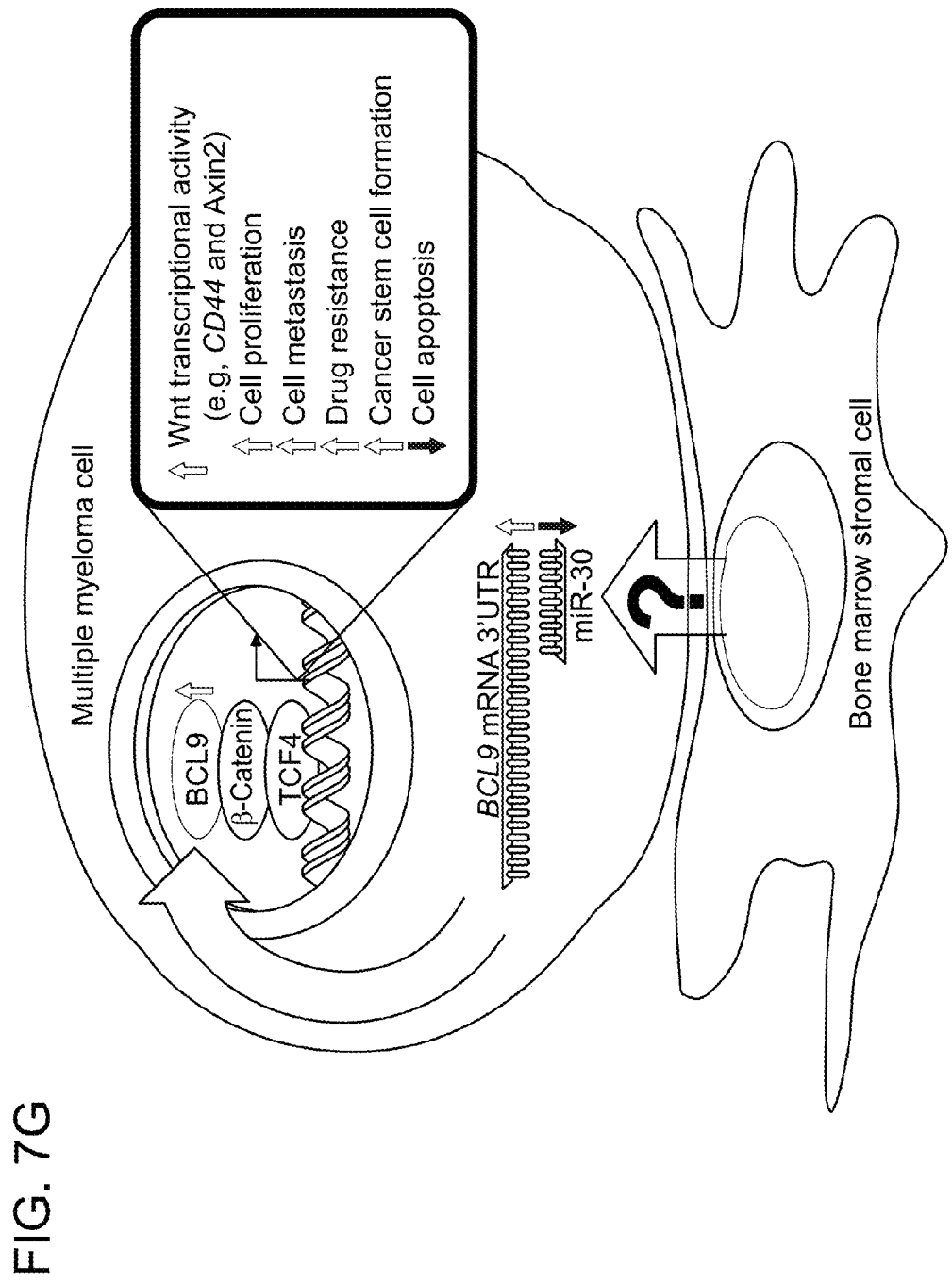
Figure 8A:
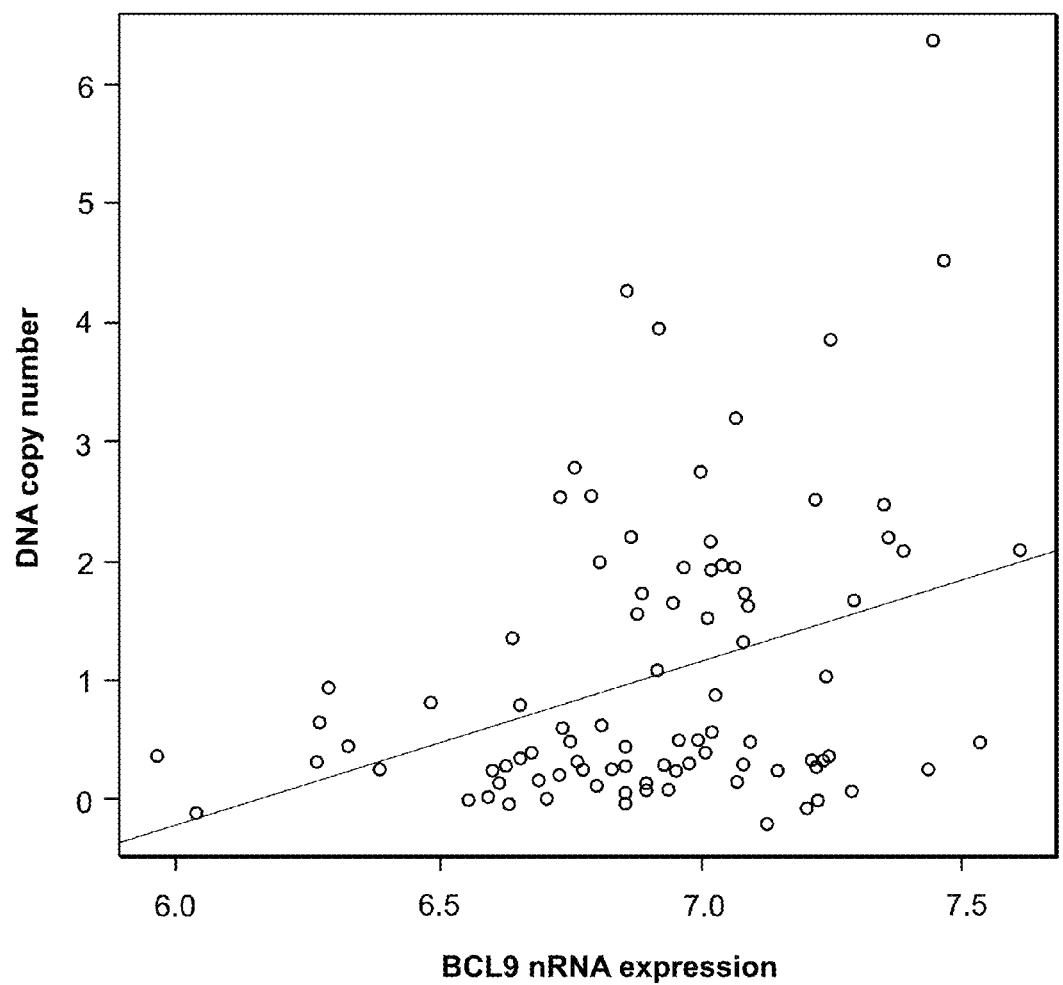
Figure 8D:
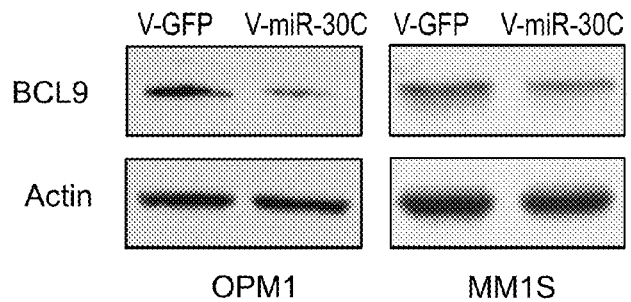
Figure 8E:
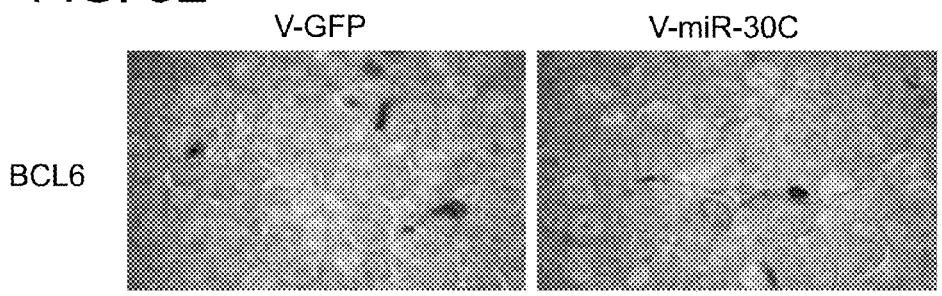
Figure 9A:
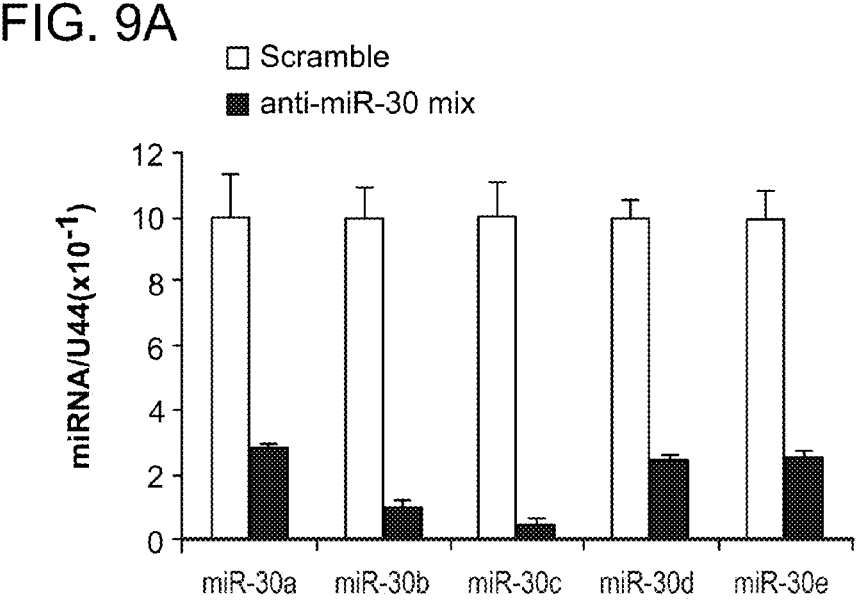
FIGS. 9A-9D show that knockdown expression of mir-30S enhances BCL9 expression in MM cells.
Figure 9C:
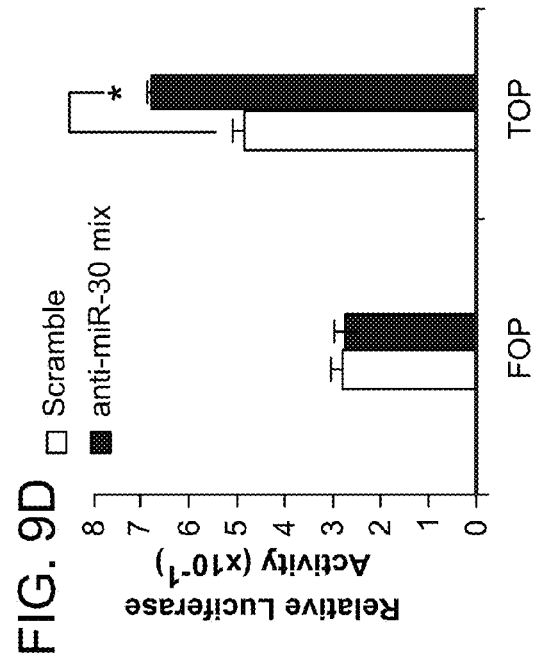
Figure 9D:
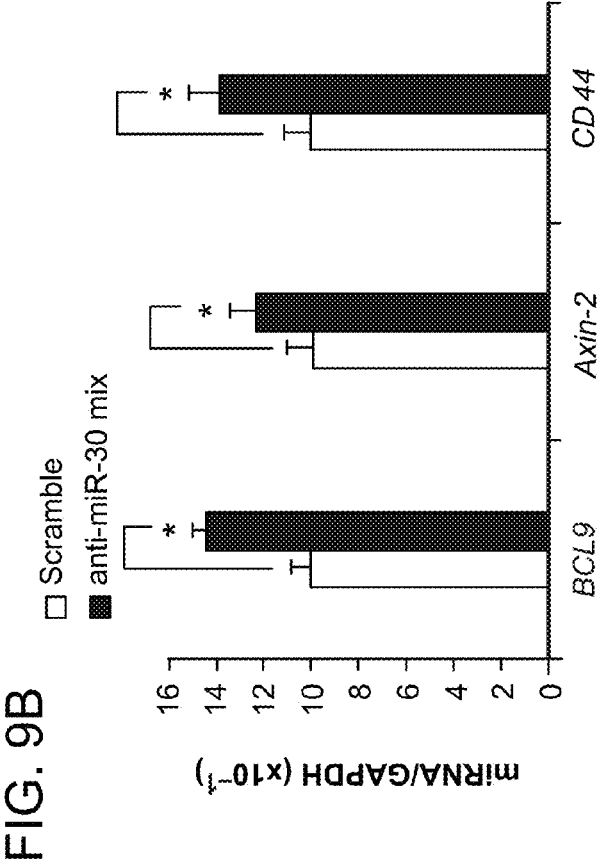
Figure 9B:
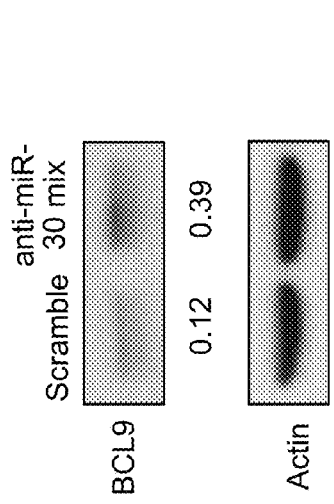
Figure 10A:
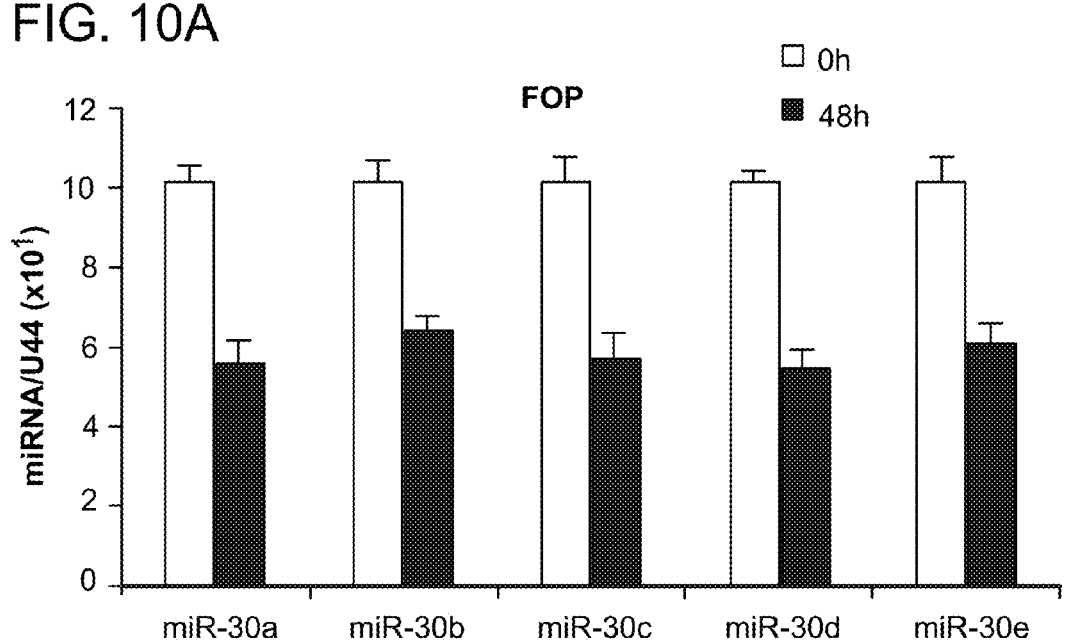
Figure 10B:
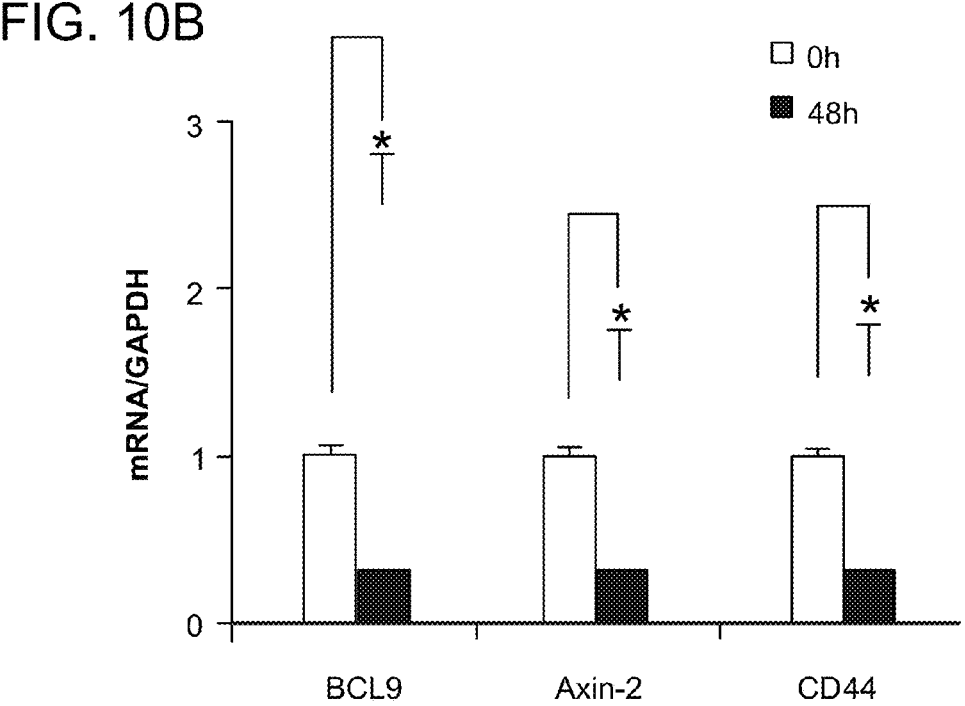
Figure 10C:
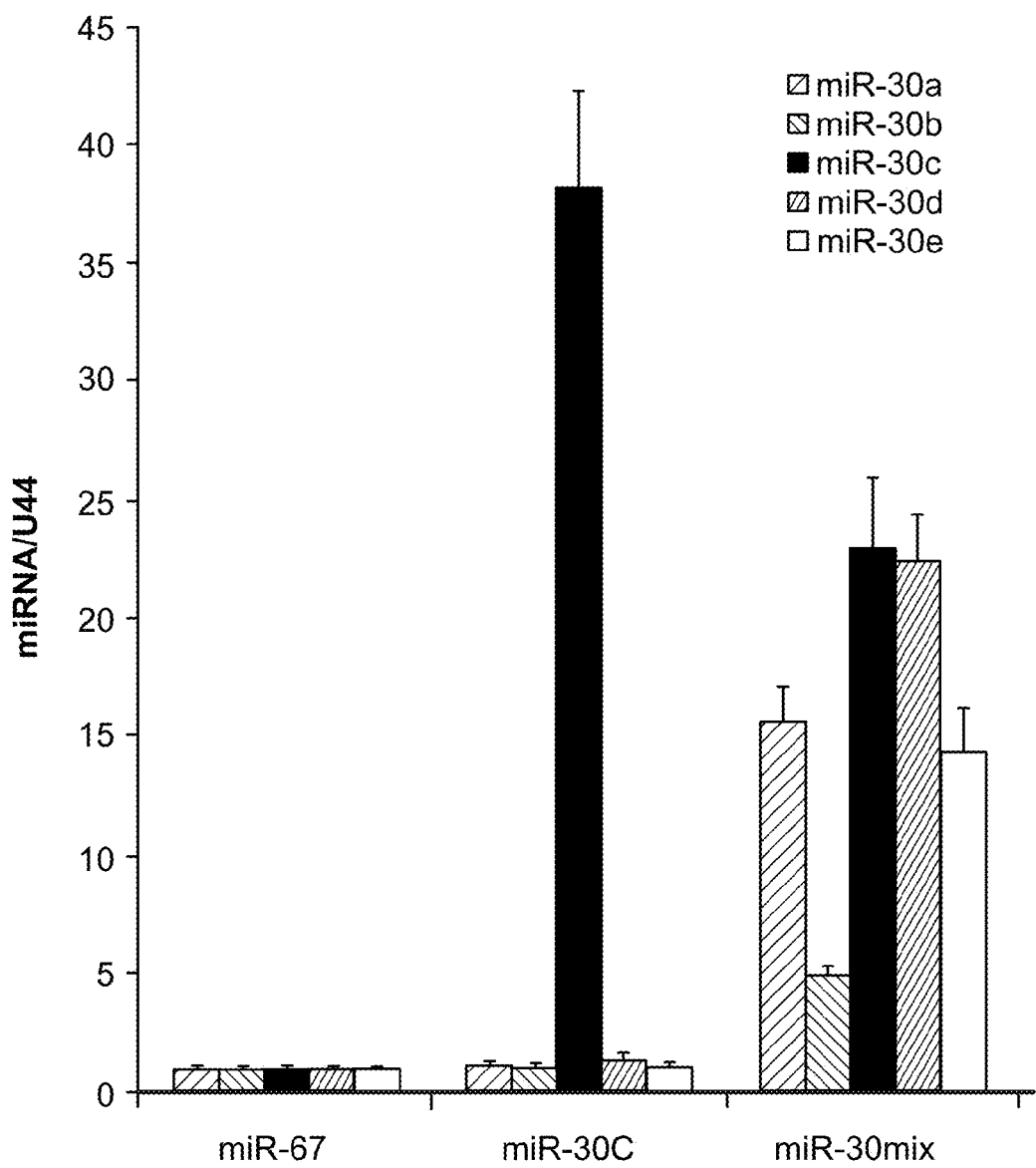
Figure 11A:
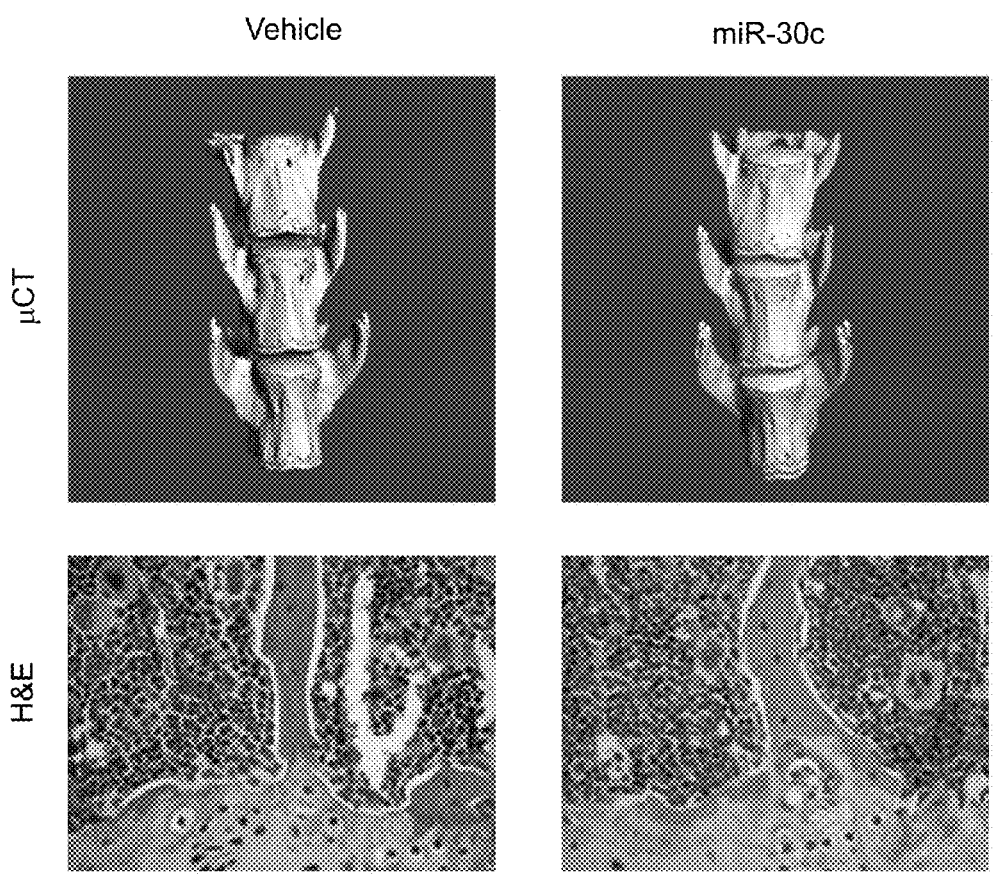
FIGS. 11A-D show that miR-30s treatment does not have a negative impact on bone disease in MM1S-Luc-Neo bearing mice.
Figure 11B:
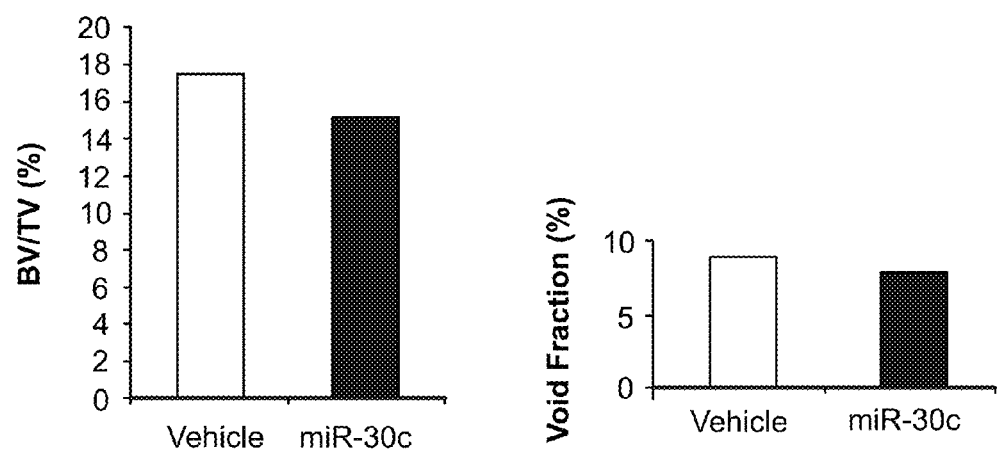
Figure 11C:
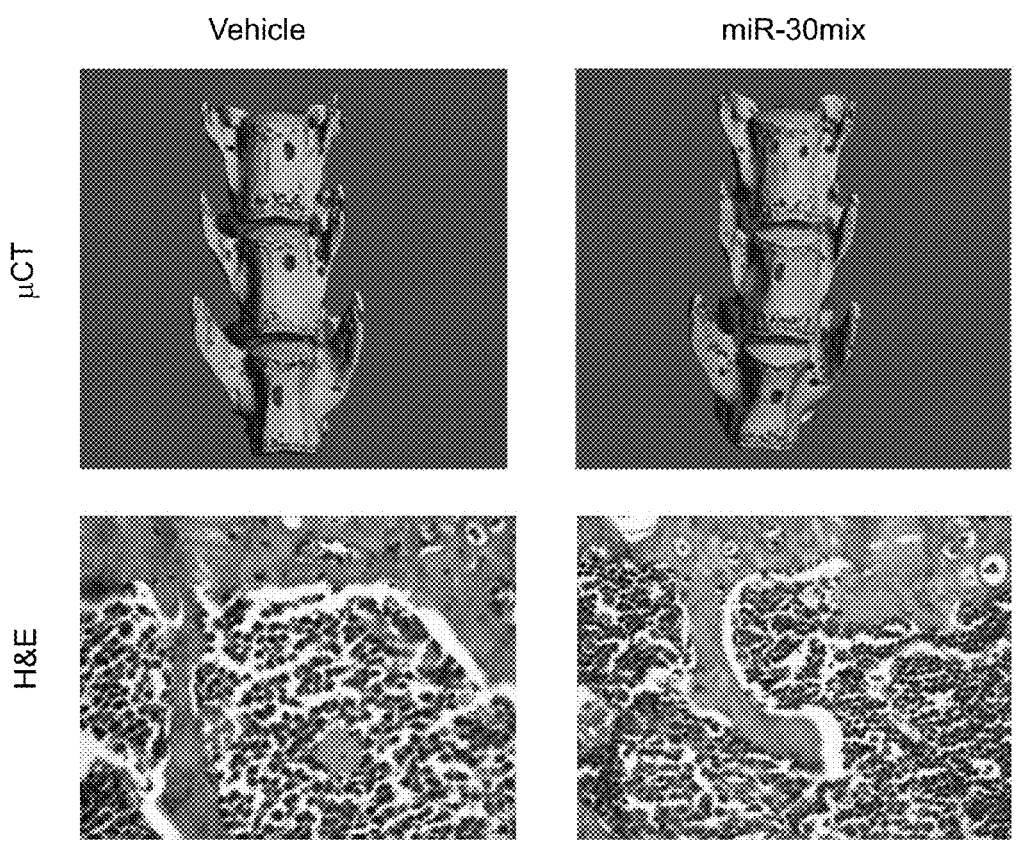
Figure 11D:
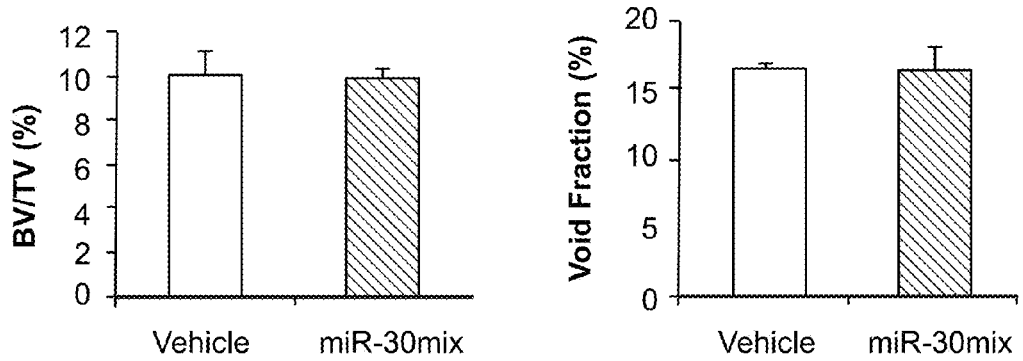

We then performed an in vivo miR-30mix delivery experiment to determine whether tumor growth is antagonized in a well established MM1S Luc-neo MM murine xenograft model of human MM (FIG. 7D-F) after i.p. delivery using lipid nanoparticles. FIG. 7D shows that survival was increased in mice treated with miR-30mix (vehicle group, 31.9±2.3 days vs. miR-30mix group, 35.7±4.4 days, n=8, p<0.05), and associated with decreased tumor burden (FIG. 7E), metastasis to the kidney (FIG. 7F, top panel), as well as decreased expression of BCL9 and CD44 proteins (FIG. 7F, bottom panel). In vivo delivery of miR-30s to target cells was confirmed using miR LNA-ISH (FIG. 7F, second row, bottom panel).

Because of the documented role of Wnt activity in bone metabolism, and the potential side effect of worsening osteolytic bone disease in myeloma patients treated with Wnt inhibitors, we evaluated the effect of miR-30s therapy in our murine xenograft model using micro-computed tomography (μCT) of bone. We first evaluated the effect of miR-30c in SCID mice not transplanted with myeloma cells. No apparent development of bone osteolytic lesions was observed in mice treated with miR-30c as compared with mice treated with vehicle. We also evaluated by μCT analysis the spines of two vehicle-treated and two miR-30mix-treated SCID mice transplanted with MM1S-Luc-Neo cells at day 21 of treatment (FIG. 7D). No major differences in trabecular bone volume and cortical void fraction were observed between mice treated with vehicle or miR-30mix. In addition, the cortical void fraction of mice transplanted with MM cells and treated with miR-30mix was similar to mice not transplanted with MM cells. Furthermore, no evidence of bone lytic lesions as evaluated histologically was observed in long bones not involved by MM cells. Overall, these results suggest that miR-30s treatment does not have a negative impact on bone. Thus, miR-30s treatment effectively inhibited BCL9-driven Wnt transcriptional activity in vivo, thereby suppressing tumor growth, invasion, and enhancing survival, highlighting the potential role of miR-30s as a novel therapeutic approach in MM. The lack of improvement in MM associated bone disease in miR-30s treatment suggested that this approach should be implemented in association with therapies that reduce osteoclast-mediated bone resorption such as bisphosphonates.

Example 10

Supplemental Data

Additional materials and methods used to carry out the examples described herein are described below.

MiRs Microarray Analysis

Total RNA was isolated using Trizol reagent (Invitrogen). MiRs profiling was performed by using Taqman miRs expression array (Applied Biosystem). Gene expression from dataset GSE27306 is normalized by RMA (Robust Multiarray Averaging) method and using refseq CDF annotation files. Processed miRs expression was used. Both linear "pearson" and non-linear one "spearman" correlation co-efficient were calculated, Correlation Test was applied to test the difference between these two independent correlation coefficients. All samples were divided based on a miR-30 member's expression into three equal-size groups (low, medium, high), followed by side-by-side boxplots of BCL9 expression, and then an ANOVA test of BCL9 expression between the 3 groups. A P-value was generated by an ANOVA test.

Cell Proliferation, Apoptosis, Invasion, and Migration Assays

Cell proliferation was assessed by [H] thymidine uptake as described (10). For apoptosis, cells were stained with Annexin-V-Fluos (Boehringer, Mannheim, Germany). Cell-Quest (Becton-Dickinson, Sunnyvale, Calif.). Cell invasion and migration assays were performed as described (22).

Soft Agar Colony Formation Assay

Cells were added to 0.35% low-melting-temperature agarose (Seaplaque) containing DMEM culture medium as described above, and transferred at a density of $0.5 \times 10^6$ cells/plate to 6 cm cell culture plates previously lined with 0.5% agar DMEM culture medium. After 15 days, the colonies were stained with 0.005% Crystal violet and counted.

SP Staining and Macrosphere Formation Assays

Hoechst 3342 SP staining was performed as described (23). SP cells (1000 cells/mL) were sorted and cultured in serum-free stem cell medium with DMEM-F12 (BioWhittaker) supplemented with B27 (1:50, Invitrogen), 20 ng/mL EGF (BD Biosciences), 0.4% BSA Sigma, and 4 μg/mL insulin (Sigma). Spheres per well (1000 corted SP cells/well) were counted after three days of culture.

Statistical Analysis

The statistical significance of differences between groups was analyzed by unpaired Student's t test. A $p<=0.05$ was considered to be statistically significant.

Mouse Xenograft Models of Tumor Burden and Metastasis $5 \times 10^6$ H929 MM cells stable transduced with V-miR-30 and V-GFP were injected subcutaneously (s.c.) or intravenously (i.v.) into hairless SCID Crl: SHO-Prkdc$^{scid}$ Hr$^{hr}$ mice (STRAIN CODE 474, Charles River), as previously described (9). All experiments involving animals were approved by DFCI Institutional Animal Care and Use Committee. For s.c. injected mice, each animal was injected in flanks, one side with V-GFP H GFP H929 cells and the other side with V-GFP H929 cells. Tumor development was measured every 3 days from first appearance, and tumor volume was calculated as Volume=(Length×Width$^2$×3.1415926)/6. Animals were euthanized when tumors reached 2 cm$^3$. For i.v. injected mice, survival was evaluated from the first day of tumor injection until death. Hind limb paralysis and tumor burden were used as an end point in the disseminated disease model, and GFP positive tumor image was captured by LAS4000 Luminescent Imager Analyzer (Fujifilm). To assess in vivo cell proliferation, apoptosis activity, and expression of downstream target genes of miR-30s, GFP-positive tumor samples were excised from the murine xenograft models for IHC analysis, as in previous studies (9).

Micro-Computed Tomography

Micro-computed topographic (μCT) imaging was performed on the L4-L6 vertebrae of the intact spine of a subset of mice using a high-resolution desktop imaging system (tCT40, Scanco Medical AG, Bruttisellen, Switzerland). Scans were acquired using a 12 μm³ isotropic voxel size, 70 kVp peak x-ray tube potential, and 200 ms integration time. Cortical and trabecular bone micro architecture was quantified in the 5$^{th}$ lumbar vertebral body in a region beginning 120 μm below the cranial growth plate and ending 120 μm above the caudal growth plate. To assess cortical lesions, we determined the cortical bone volume (Ct.BV) and total volume (Ct.TV) of the ventral face of the vertebral body. Cortical void fraction (%) was calculated as 1−(Ct.BV/Ct.TV)*100 and represents the percent of the ventral face that was void of bone. Trabecular bone volume fraction (Tb.BV/Tb.TV,%) was measured in the region of interest. In NOD/SCID mice not transplanted with myeloma cells, μCT was performed in one mouse treated with vehicle and one mouse treated with miR-30c after 10 days of treatment. In NOD/SCID mice transplanted with myeloma cells, μCT was performed in two selected mice (showing spine involvement by whole body imaging) for each experimental group at day 21 of treatment.

It is to be understood that the foregoing description is intended to illustrate and not to limit the scope of the invention, which is defined by the scope of the appended claims. Other embodiments are within the scope of the following claims.

The invention claimed is:

1. A method for inhibiting BCL9 expression in a population of B cells in a first subject, the method comprising administering to the first subject a therapeutically effective amount of an agent comprising an miR-30 polynucleotide, wherein the population of B cells have a higher amount of BCL9 RNA or protein than a corresponding population of B cells from a second subject and wherein the second subject does not have multiple myeloma.

2. The method of claim 1, wherein the administration of the agent decreases the amount of BCL9 RNA or protein in the population of B cells.

3. The method of claim 1, wherein the population of B cells are sensitive to inhibition of a Wnt signaling pathway.

4. The method of claim 1, wherein the miR-30 polynucleotide comprises a ribonucleic acid.

5. The method of claim 1, wherein the miR-30 polynucleotide comprises a deoxyribonucleic acid.

6. The method of claim 1, wherein the miR-30 polynucleotide comprises one or more non-naturally occurring polynucleotides.

7. The method of claim 6, wherein the non-naturally occurring nucleotide is a 2'-O-methyl oligoribonucleotide.

8. The method of claim 1, wherein the miR-30 polynucleotide comprises a polynucleotide that hybridizes specifically to one or more sequence motifs selected from the group consisting of SEQ ID NOs: 33 and 34.

9. The method of claim 1, wherein the miR-30 polynucleotide comprises a motif having the nucleic acid sequence of SEQ ID NO: 36.

10. The method of claim 1, wherein the miR-30 polynucleotide comprises a polynucleotide comprising one or more sequences selected from the group consisting of SEQ ID NOs: 1-5.

11. The method of claim 1, wherein the agent further comprises a nanoparticle.

12. The method of claim 1, wherein the agent further comprises a lipid.

13. The method of claim 11, wherein the nanoparticle is a lipid nanoparticle.

14. The method of claim 1, wherein the agent further comprises a viral vector.

15. The method of claim 14, wherein the viral vector is a lentiviral vector, an adenoviral vector, an adeno-associated viral vector, or a retroviral vector.

16. The method of claim 1, wherein the agent further comprises a plasmid.

17. The method of claim 1, wherein the agent is administered intravenously or subcutaneously.

18. The method of claim 1, wherein the subject has or is at risk for monoclonal Gammopathy of Undetermined Significance (MGUS), smoldering myeloma, asymptomatic MM, or symptomatic MM.

19. The method of claim 18, wherein the symptomatic MM is newly diagnosed MM.

20. The method of claim 18, wherein the symptomatic MM is late stage relapsed/refractory MM.

21. The method of claim 1, further comprising administering an additional anti-cancer therapy to the subject.

22. The method of claim 21, wherein the additional anti-cancer therapy is selected from the group consisting of surgery, chemotherapy, radiation, hormone therapy, immunotherapy, and a combination thereof.

23. The method of claim 21, wherein the additional anti-cancer therapy reduces bone absorption.

24. The method of claim 21, wherein the additional anti-cancer therapy reduces osteoclast mediated bone resorption.

25. The method of claim 23, wherein the additional anti-cancer therapy is a bisphosphonate.

26. The method of claim 1, wherein the subject is a human.

27. A method of reducing proliferation, survival, migration, or colony formation ability of multiple myeloma cells in a subject with multiple myeloma, the method comprising administering to the subject a therapeutically effective amount of an agent comprising an miR-30 polynucleotide, wherein the multiple myeloma cells have a higher amount of BCL9 RNA or protein than normal plasma cells.

28. A method of inhibiting metastasis of multiple myeloma in a subject in need thereof, the method comprising administering to the subject a therapeutically effective amount of an agent comprising an miR-30 polynucleotide, wherein the multiple myeloma cells have a higher amount of BCL9 RNA or protein than normal plasma cells.

29. A method of treating a hematological malignancy in a subject in need thereof, the method comprising administering to the subject a therapeutically effective amount of an agent comprising an miR-30 polynucleotide, wherein the hematological malignant cells have a higher amount of BCL9 RNA or protein than normal hematological cells.

30. The method of claim 29, wherein the hematological malignancy is selected from the group consisting of myelodysplastic syndrome, Hodgkin's lymphoma, chronic lymphocytic leukemia, and B cell lymphoma.

31. The method of claim 9, wherein the miR-30 polynucleotide comprises insertion, deletion or substitution of one or more nucleotides in a sequence selected from the group consisting of SEQ ID NOs: 1-5.

* * * * *